(12) United States Patent
O'Kennedy

(10) Patent No.: US 10,973,865 B2
(45) Date of Patent: Apr. 13, 2021

(54) METHOD OF MAKING SOLANACEAE FRUIT EXTRACTS

(71) Applicant: Provexis Natural Products Limited, Reading (GB)

(72) Inventor: Niamh O'Kennedy, Reading (GB)

(73) Assignee: Provexis Natural Products Limited, Reading (GB)

( * ) Notice: Subject to any disclaimer, the term of this patent is extended or adjusted under 35 U.S.C. 154(b) by 166 days.

(21) Appl. No.: 15/866,900

(22) Filed: Jan. 10, 2018

(65) Prior Publication Data

US 2018/0256666 A1    Sep. 13, 2018

Related U.S. Application Data

(63) Continuation of application No. 14/030,533, filed on Sep. 18, 2013, now abandoned, which is a continuation of application No. 13/124,512, filed as application No. PCT/GB2009/002593 on Nov. 2, 2009, now abandoned.

(30) Foreign Application Priority Data

Oct. 31, 2008  (GB) .................................. 0819959

(51) Int. Cl.
*A61K 36/81* (2006.01)
*A61K 31/7048* (2006.01)
*A61K 31/7064* (2006.01)

(52) U.S. Cl.
CPC .......... *A61K 36/81* (2013.01); *A61K 31/7048* (2013.01); *A61K 31/7064* (2013.01)

(58) Field of Classification Search
CPC ..................................................... A61K 36/81
See application file for complete search history.

(56) References Cited

U.S. PATENT DOCUMENTS

| | | | |
|---|---|---|---|
| 4,925,690 A | 5/1990 | Odake | |
| 5,502,038 A | 3/1996 | Malinow | |
| 6,436,452 B1 * | 8/2002 | Deutz | A23L 19/09 426/52 |
| 6,958,164 B2 | 10/2005 | Dutta-Roy | |
| 2003/0206983 A1 | 11/2003 | Dutta-Roy | |
| 2004/0191790 A1 | 9/2004 | Tomassen et al. | |
| 2004/0223962 A1 | 11/2004 | Riordan | |
| 2005/0153038 A1 | 6/2005 | Giori | |
| 2006/0078632 A1 | 4/2006 | Woo et al. | |
| 2006/0084614 A1 | 4/2006 | Eckl et al. | |
| 2006/0154877 A1 | 7/2006 | Liu et al. | |
| 2007/0259059 A1 | 11/2007 | Eidenberger | |
| 2008/0009449 A1 | 1/2008 | Prasad | |
| 2009/0053340 A1 | 2/2009 | Crosbie et al. | |
| 2009/0123584 A1 | 5/2009 | O'Kennedy | |
| 2011/0206794 A1 | 8/2011 | O'Kennedy | |
| 2011/0212913 A1 | 9/2011 | O'Kennedy | |
| 2012/0321732 A1 | 12/2012 | O'Kennedy | |
| 2014/0147537 A1 | 5/2014 | O'Kennedy | |
| 2015/0105338 A1 | 4/2015 | O'Kennedy | |

FOREIGN PATENT DOCUMENTS

| | | |
|---|---|---|
| CN | 1352941 | 6/2002 |
| CN | 1650951 | 8/2005 |
| DE | 19720767 A1 | 11/1998 |
| EP | 1334728 A2 | 8/2003 |
| EP | 1481669 A1 | 12/2004 |
| EP | 1508325 A1 | 2/2005 |
| EP | 1559421 A1 | 8/2005 |
| EP | 1640001 A1 | 3/2006 |
| FR | 2871378 A1 | 12/2005 |
| JP | 050201846 | 8/1993 |
| JP | 03004769 | 1/1999 |
| JP | 2007037530 | 2/2007 |
| JP | 2004315386 A | 10/2007 |
| WO | WO 99/55350 A1 | 11/1999 |
| WO | WO 00/21507 A2 | 4/2000 |
| WO | WO 2006085115 | 8/2006 |
| WO | WO 06/094120 A1 | 9/2006 |
| WO | WO 2007/141495 | 6/2007 |
| WO | WO 08/080162 A2 | 7/2008 |
| WO | WO 08/131047 A2 | 10/2008 |
| WO | WO 2010/049709 A2 | 5/2010 |
| WO | WO 2010/049707 A2 | 12/2016 |

OTHER PUBLICATIONS

Franklin, SJ. GRAS Exemption Claim Claim of Exemption From the Requirement for Premarket Approval Pursuant to Proposed 21 CFR § 170.36(c)(1) (62 FR 18938(Apr. 17, 1997)) for Water-Soluble Tomato Concentrate (WSTC). Prepared by Provexis. Aug. 14, 2006. 74 pages. (Year: 1997).*

The Wor;d's Healthiest foods: can you tell me about the acitidy of tomatoes? Internet archive date: Sep. 19, 2015. Retrieved from the Internet on: Apr. 11, 2020. Retrieved from: <URL: https://web.archive.org/web/20150919145114/http://whfoods.org/genpage.php?tname=dailytip&dbid=383>. (Year: 2015).*

Abushita et al., Determination of Antioxidant Vitamins in Tomatoes. Food Chemistry (1997), 60(2):207-212.

(Continued)

*Primary Examiner* — Amy L Clark
(74) *Attorney, Agent, or Firm* — Nixon Peabody LLP; Linda B. Huber

(57) ABSTRACT

Provided are methods of making an extract of fruit of the Solanaceae family wherein fruit is processed to optimise the platelet aggregation inhibiting activity of the extract. The methods involve preparing a start mix of homogenised fruit; separating a water soluble fraction from fruit solids; filtration of the water soluble fraction; and concentration of active agents in the filtration permeate. The invention also provides fruit extracts manufactured by such methods, and also fruit extracts containing glycosylated phenolic acid or a phenolic ester, or derivatives thereof, a glycosylated flavonoid; and a nucleoside. The extracts of the invention are useful as medicaments for the treatment or prevention of a medical condition characterised by inappropriate platelet aggregation. In particular, the medicaments may be of use in maintaining heart health by reducing platelet aggregation; benefiting the circulation, and/or normalizing or otherwise benefiting blood flow.

5 Claims, 10 Drawing Sheets

(56) References Cited

OTHER PUBLICATIONS

Van Het Hof et al., Carotenoid bioavailability in humans from tomatoes processed in different ways determined from the carotenoid response in the triglyceride-rich lipoprotein fraction of plasma after a single consumption and in plasma after four days of consumption. Journal of Nutrition (2000), 130:1189-1196.
Bohm et al., Intestinal absorption of lycopene from different matrices and interactions to other carotenoids, the lipid status, and the antioxidant capacity of human plasma. European Journal of Nutrition (1999), 38(2):1436-6207. Abstract Only.
Friedman et al., Feeding tomatoes to hamsters reduces their plasma low-density lipoprotein cholesterol and triglycerides. Journal of Food Science (2000), 65(5):897-900. Abstract Only.
PCT/GB2007/002034 International Preliminary Report on Patentability dated Dec. 3, 2008; 8 pages.
PCT/GB2006/000521 International Search Report and Written Opinion dated Aug. 10, 2006; 9 pages.
PCT/GB2006/000521 International Preliminary Report on Patentability dated Aug. 14, 2007; 7 pages.
PCT/GB2007/002034 International Search Report and Written Opinion dated Oct. 29, 2007; 10 pages.
Dutta-Roy et al., Effects of tomato extract on human platelet aggregation in vitro. Platelets (2001), 12(4):218-227.
Hsiao G. et al., Inhibitory effects of lycopene on in vitro platelet activation and in vivo prevention of thrombus formation. Journal of Laboratory and Clinical Medicine (2005), 146(4):216-226.
Yamamoto et al., Tomatoes have natural anti-thrombotic effects. British Journal of Nutrition (2003), 90(6):1031-1038.
Maruyama et al. Therapeutic strategy targeting coagulation factor Xa in thromboemobolism—Antithrombotic therapy by targeting Xa. Journal of Clinical and Experimental Medicine (2004). 208:393-395.
Yokoyama et al. New anti-platelet drug and anticoagulation drug—Differences from asprin, warfarin and heparin. Journal of Clinical and Experimental Medicine (2006). Supp vol. (Apoplexy): 17-22.
PCT/GB2009/002593 International Search Report and Written Opinion dated Aug. 10, 2011.
PCT/GB2009/002593 International Preliminary Report on Patentability dated Oct. 11, 2011.
Miean et al., Flavonoid (myricetin, quercetin, kaempferol, luteolin, and apigenin) content of edible tropical plants. Medicinal & Aromatic Plants Abstracts. 2002, 24(1).
Naczk et al., Pheolics in cereals, fruits and vegetables: Occurrence, extraction and analysis. Journal of Pharmaceutical and Biomedical Analysis. 2006, 41(5):1523-1542. Abstract.
Slimestad et al., The Flavonoids of Tomatoes, 2008, Journal of Agricultural and Food Chemistry, vol. 56(7):2436-2441.
O'Kennedy et al., Effects of antiplatelet components of tomato extract on platelet function in vitro and ex vivo: a time-course cannulation study in healthy humans. American Journal of Clinical Nutrition (2006), 84(3):570-579.

O'Kennedy et al., Effects of tomato extract on platelet function: a double-blinded crossover study in healthy humans. American Journal of Clinical Nutrition (2006), 84(3): 561-569.
Stevenson et al., Comparison of the relative recovery of polyphenolics in two fruit extracts from a model of degradation during digestion and metabolism. Molecular Nutrition & Food Research. 2007, 51(8):939-945.
Zheng et al., Oxygen radicals absorbing capacity of phenolics in blueberries, cranberries, chokeberries, and lingonberries. Journal of Agricultural and Food Chemistry. 2003, 51(2).
Hwang et al., Effects of tomato paste extracts on cell proliferation, cell-cycle arrest and apoptosis in LNCaP human prostate cancer cells. BioFactors. 2005, 23:75-84.
Franklin, S.J., GRAS Exemption Claim: Claim of Exemption from the Requirement for Premarket Approval Pursuant to Proposed 21 CFR Section 170.36 (c)(1) [62 FR 18938 (Apr. 17, 1997) for Water-Soluable Tomato Concentrate (WSTC), Prepared by Provexis, 2006, 74 pages.
PCT/GB2009/002595 International Preliminary Report on Patentability dated May 3, 2011; 18 pages.
PCT/GB2009/002595 International Search Report and Written Opinion dated Apr. 26, 2010; 25 pages.
Moco et al. A Liquid Chromatography-Mass Spectrometry-Based Metabolome Database for Tomato. Plant Physiology (2006). 141:1205-1218.
Oliff, H. Scientific and Clinical Monograph for Pycnogenol. Retrieved from internet: http://abc.herbalgram.org/site/DocServer/Pycnog_FullMono120809_LOW.pdf?docID=1741 on Jan. 1, 2010.
Lopez et al., Deep venous thrombosis. American Society of Hematology (2004), 439-456.
Anthon et al., Thermal inactivation of pectin methylesterase, polygalacturonase, and peroxidase in tomato juice. Journal of Agriculture and Food Chemistry (2002), 50:6153-6159.
Exam Report of EP Application No. 07733050.4, dated Jan. 13, 2012, 7 pages.
Jerjes-Sanchez, C. Venous and arterial thrombosis: a continuous spectrum of the same disease? European Heart Journal. (2005) 26(1):3-4.
Weber M. et al. Enhance platelet aggregation with TRAP-6 and collagen in platelet aggregometry in patients with venous thromboembolism Thrombosis Research. (2002) 107(6):325-328.
Zhu T. et al. Three-Dimensional Reconstruction of Thrombus Formation during Photochemically Induced Arterial and Venous Thrombosis. Animals of Biomedical Engineering Society. (2003) 31(5):515-525.
Hua, J. Diagnosis and Treatment of Deep Venuous Thrombosis Formation in the Lower Limbs (with Analysis of 73 Cases). Zhejiang Medical Journal (1991). 13(6): 3-5.
Zhuang, Q. Blood Coagulation and Fibrinolysis. Chinese Journal of Medicine (1981). 2(11):10-13.
Roth, GJ. Platelets and blood vessels: the adhesion event. Immunology Today (1992). 13(3):100-105.
Longo et al. Extract from Harrison's Principals of Internal Medicine. McGraw Hill Companies, Inc. 18th Edition (2012). 9 pages.
Martini et al. Extract from Fundamentals of Anatomy and Physiology. Blood (2009) 8th Edition. Ch. 11. pp. 262-263.

* cited by examiner

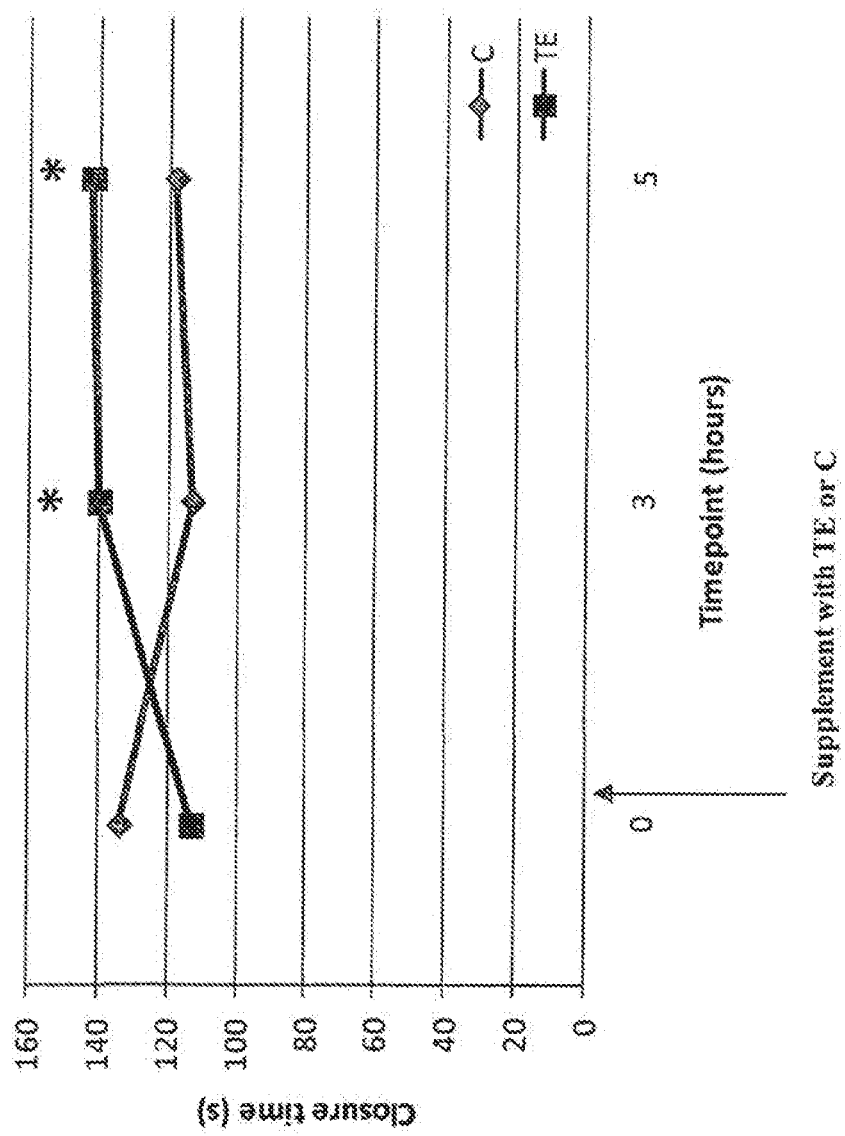

METHOD OF MAKING SOLANACEAE FRUIT EXTRACTS

CROSS-REFERENCE TO RELATED APPLICATIONS

This application is a continuation of U.S. patent application Ser. No. 14/030,533 filed Sep. 18, 2013, which is a continuation of application Ser. No. 13/124,512, filed Apr. 15, 2011, which is the National Phase of International Application PCT/GB2009/002593, filed Nov. 2, 2009 which designated the U.S. and that International Application was published under PCT Article 21(2) in English. This application also includes a claim of priority under 35 U.S.C. § 119(a) and § 365(b) to British patent application No. GB 0819959.8, filed Oct. 31, 2008.

The present invention relates to a fruit extract that prevents platelet aggregation and is useful as an antithrombotic agent and methods of making such extracts.

It is well established that consumption of fruits and vegetables is an important preventative measure by which the risk of cardiovascular diseases can be reduced. Accordingly considerable effort has been expended in an attempt to identify compounds derived from fruits and vegetables that have a role in the prevention of heart disease.

Particular interest has been shown in agents that inhibit platelet aggregation. When platelets aggregate within the circulatory system, thrombi are formed which are large enough to block blood vessels. However before full aggregation takes place, platelets can circulate in an activated condition. When in this state, platelet stickiness is greatly increased, and they can stick to each other, to other blood cells, or to components of the blood such as lipid-rich chylomicrons. This causes micro-aggregates to form, and lowers the fluidity of the blood, affecting blood flow locally, and the circulation systemically. Reducing platelet aggregability helps to maintain the blood in a fluid and low-coagulable state. This helps to normalize blood flow, by preventing micro-aggregates from forming within the circulation, and by preventing the adherence of platelets to blood vessel walls or fatty plaques.

In the light of this will be recognized that agents able to inhibit platelet aggregation are of use in preventing coronary disease, for example myocardial infarctions and stroke and in preventing further thrombo-embolic events in patients who have suffered myocardial infarction, stroke or unstable angina. In addition, such agents may be of use in preventing restenosis following angioplasty and bypass procedures. Moreover, these agents may be of use in the treatment of coronary disease resulting from thrombo-embolic disorders such as myocardial infarction in conjunction with thrombolytic therapy.

There are many known anti-platelet-aggregation agents that act at different stages of platelet production and action. Aspirin (acetylsalicylic acid) is the most widely used and studied. Dipyridamole and ticlopidine have also been used. Aspirin's antiplatelet activity is due to irreversible inhibition of platelet cyclo-oxygenase, thus preventing the synthesis of thromboxane A2, a compound that causes platelet aggregation. Indobufen is a reversible inhibitor of platelet cyclo-oxygenase. Some compounds are direct inhibitors of thromboxane A2 synthase, for example pirmagrel, or act as antagonists at thromboxane receptors, for example sulotroban.

International Patent application WO 99/55350 discloses that water-soluble extracts from a number of fruits exhibit an ability to inhibit platelet aggregation. It was considered surprising that anti-platelet-aggregation activity was found to be water soluble because, in contrast, active extracts known to the art at that time were lipid soluble compounds (e.g. lycopene). These water-soluble extracts were found to have significant efficacy for preventing or reducing platelet aggregation and have been marketed, with Food Standards Agency approval in Europe, as a nutritional supplement with health benefits.

The active component of the WO 99/55350 fruit extract was analysed by mass spectroscopy (MS) and nuclear magnetic resonance (NMR) spectroscopy and found to contain a mixture of nucleosides having platelet aggregation inhibiting activity.

The present invention is based upon the inventor's realisation that nucleosides, within water-soluble fruit extracts, may not be the only compounds within such extracts that prevent anti-platelet aggregation. They therefore exerted considerable effort to further fractionate and characterize the active agents within water-soluble extracts described in WO 99/55350 in an attempt to improve the efficacy of such extracts for inhibiting platelet aggregation and develop new methods of processing fruit for such a use.

It has now been found that fruits of the Solanaceae family, may be processed in ways that result in water-soluble extracts that have an optimised beneficial effect on platelet aggregation. This new knowledge has enabled the inventors to develop new fruit extracts, and methods of making the same, with efficacy for inhibiting platelet aggregation.

Thus according to a first aspect of the invention there is provided a method of making an extract of fruit of the Solanaceae family wherein fruit is processed to optimise the platelet aggregation inhibiting activity of the extract comprising the steps of:

(a) Preparing a start mix of homogenised fruit;
(b) Separating a water-soluble fraction from fruit solids;
(c) filtration of the water-soluble fraction; and
(d) concentration of active agents in the filtration permeate The inventors decided to analyse the active compounds in the fruit extracts described in WO 99/55350 (see Example 1). The inventors were surprised to find that a number of compounds, found naturally in plants, were effective for inhibiting platelet aggregation. This lead them to realise that the methods described in WO 99/55350 may be adapted to develop methods that will result in extracts in which the content of such active agents is maintained (i.e. minimal amounts of the active compound are lost during the processing of the fruit) or the active agents are actually enriched in the production of a fruit extract. After much trial and error they established that the steps according to the method of the first aspect of the invention results in fruit extracts that are effective for reducing platelet aggregation and comprise a number of active, water soluble compounds found in the fruit.

(a) Preparing a Start Mix

The flesh of whole fruit, preferably tomatoes, is homogenised, with or without the skin of the fruit to form a paste. Alternatively, commercially available tomato pastes may be used as the starting material for the preparation of the start mix. Where the starting material for the preparation of the extracts is a tomato paste, it is preferably one that has been produced by means of a "cold-break" process rather than a "hot-break" process. The terms "cold-break" and "hot-break" are well known in the field of tomato processing and commercially available tomato pastes are typically sold as either hot-break or cold-break pastes. Cold-break pastes can be prepared by a process involving homogenisation of the tomato followed by a thermal processing step in which the tomatoes are heated to temperatures of no more than about 60° C., in contrast to hot-break pastes where the homogenised tomatoes are subjected to thermal processing at temperatures of about 95° C., see for example, Anthon et al., *J. Agric. Food Chem.* 2002, 50, 6153-6159.

The thickness of such pastes (whether from fresh fruit or a commercially available paste) should be adjusted by diluting with water or an aqueous solution (preferably demineralised water) to form a "start mix". The inventors have found that optimal activity is achieved in the final fruit extract if the start mix is diluted such that it contains less than 33% solids and more preferably less than 20% solids. In one preferred embodiment of the invention the start mix comprises between about 10 and 15% solids (e.g. 13% solids).

The inventors have found that the holding temperature of the start mix can have a significant effect on the activity of the extract. It is therefore preferred that the holding temperature does not exceed 35° C. and more preferably does not exceed 30° C.

The inventors have also found that the pH of the start mix also impacts on the activity of the extract prepared according to the method of the invention. The pH of the mix should be acidic; preferably less than pH 5.5 and in a preferred embodiment the pH should not rise above 4.2. Adjustments to pH, if required, may be made by addition of citric acid.

Furthermore the inventors have found that the browning index of the start mix should also be controlled to optimise activity of the finial extract. Accordingly the browning index of the start mix, defined as the absorbance of the soluble portion at 420 nm, preferably does not exceed 0.4 AU at 4% solids. Browning index is an index of visible browning caused by formation of melanoidins (polymeric conjugates of variable composition, based on sugars and amino acids) and may be measured by centrifuging a 50 mL sample of the start mix at 3500 rpm for 10 minutes at room temperature, removing a portion of the supernatant, diluting it to 4% solids as measured by refractometer, and measuring the absorbance of this solution at 420 nm in a spectrophotometer.

The inventors have found that fruit extracts according to the method of the invention have improved anti-aggregation activity if at least one of the temperature, pH and browning index are controlled in the start mix as discussed above. It is preferred that at least two of these control steps (e.g. temperature and pH; or temperature and browning index) are controlled and more preferred that the temperature, pH and Browning index are controlled as discussed above.

It is most preferred that the start mix is maintained at a temperature that is no higher than 30° C.; at a pH of less than 4.2 and with a browning index that does not exceed 0.4 AU.

(b) Separating a Water-Soluble Fraction from Fruit Solids.

Water-insoluble solids may be removed from a water-soluble fraction by using a number of standard techniques.

It is preferred that this step in the methodology removes large-sized (i.e. particle size >500µ) water insoluble solids from the start mix.

Such solids may be removed by use of:
(a) a decanter (e.g. a Westfalia GEA decanter);
(b) a centrifugal separation step (e.g. a rotating disc centrifuge); or
(c) a separator containing size-adjustable nozzles (e.g. a Westfalia MSB-15 separator, using a mixture of blanks and nozzles sized 0.45).

Alternatively the solids may be allowed to settle and the water-soluble fraction simply decanted manually.

Whichever method is used, the inventors have found that for retention of optimal bioactivity in the water-soluble fraction, the operating temperatures should not exceed 60° C. Furthermore it is preferred that the flow rate through the equipment must be such that exposure to this 60° C. temperature does not occur for longer than 60 seconds.

The resulting water-soluble fraction should ideally be cooled after the separation step. When the fraction is to be stored it is preferred that, following separation, it is immediately cooled to <8° C.

In preferred embodiments of step (c) of the method of the invention a decanter may be used, with running temperatures of 40-45° C.

Optionally the separation step may be followed by a second clarification step (e.g. using an Alfa Lavaal Clarifier) to produce a clarified water-soluble fraction where all remaining insoluble material has a particle size <500µ and spin-down solids (i.e. material which is visibly precipitated by centrifugation at 3500 rpm for 10 minutes at room temperature) comprise <1% of the fraction by volume.

The inventors have found that the final product retains the maximum active component concentration if the clarified fraction (however produced) contains less than 10% total solids and more preferably about 8% solids or less.

(c) Filtration of the Water-Soluble Fraction

To remove very fine particulate matter (<500µ) (e.g. protein and large polymeric material such as some pectins), the water-soluble fraction should then be filtered and the permeate retained.

Filtration may be accomplished in a single stage, or in a series of filtration steps, starting with a relatively coarse filtration step to remove larger particles of tomato skin and/or other water-insoluble fragments of tomato flesh. Further filtration steps may then be effected to give a substantially clear solution, e.g. a solution that will pass through a 0.2µ filter without loss of solids.

In a preferred embodiment step (c) of the method of the invention comprises a microfiltration step using a filtration unit with ceramic membrane filters (e.g. a Tetra Alcross cross-filtration MF unit equipped with ceramic membrane filters (e.g. Pall Membralox P19-30 multi-element units)). Spiral-wound membranes may also be used as an alternative to ceramic membranes.

Ultrafiltration may also be used as an alternative to microfiltration. A range of pore sizes is acceptable, e.g. 1.4µ, 0.1µ; but the inventors have found that maximum enrichment of the filtration permeate with bioactive components (i.e. minimum losses of bioactive components and maximum exclusion of non-bioactive components) occurs when pore sizes of 0.1µ are used.

In order to retain optimal bioactivity, temperatures should not rise above 35° C. during this filtration step, and the filtration permeate should be immediately cooled to <8° C. after exiting the filtration membrane. The browning index of the final permeate should not exceed 0.4 AU.

The inventors have found that maximum recovery of bioactive components, and enrichment of the filtration permeate in bioactive components (relative to the unfiltered material), occurs when the starting unfiltered material contains <10% solids, and when the final permeate contains approximately 7% solids and has a browning index <0.4 AU.

Removal of the solids according to steps (a) to (c) has the effect of removing fragments of skin and seeds, large molecular weight proteins and pectins, and carotenoids such as lycopene/other lipids which are stabilised in droplets within the aqueous solution by the presence of pectins and proteins. Thus, the methods provide ways of preparing tomato extracts that are water soluble extracts and are also substantially free of lycopene.

The methods described, in particular the careful control of the length of exposure to temperatures >35° C. (preferably >30° C.), also ensure that the lycopene-free water-soluble extracts prepared have not been subject to degradative chemical reactions which result in the production of visible browning (Maillard reactions), as demonstrated by the browning index value of <0.4 AU. This ensures that the formation of amino acid—sugar complexes and melanoidin polymers, which can sequester some of the bioactive components, are kept to a minimum. Thus the methods described result in extracts which are optimised for bioactive component content.

In one preferred embodiment of the method of the invention, the tomato extract is a water-soluble extract substantially free of lycopene and capable of passing through a 0.2μ filter without loss of solids, and with a browning index value <0.4 AU.

(d) Concentration of Active Agents in the Filtration Permeate

The aqueous filtrate is then subjected to further concentration/fractionation steps to provide a bioactive concentrate containing compounds responsible for inhibiting platelet aggregation.

After much experimentation the inventors established that the concentration steps required careful control if peak bioactivity of the final extract was to be retained or enrichment of bioactives is to be achieved in the final concentrated product. The reason for this was found to be, that the progress of heat- and pH-dependent degradative reactions is accelerated as solids concentration increases. They therefore realised that temperature control, and length of exposure to temperature, was more crucial for concentrated extracts than for dilute extracts.

Several methods may be used to concentrate/enrich the water-soluble material—provided that the temperature of the extract is not allowed to rise such that degradation of active agents within the extract is not allowed to rise above about 60° C. for dilute fractions and below 40° C. for more concentrated samples.

Concentration Using Evaporation Techniques

Evaporation of the solution under reduced pressure may be used, under conditions where temperatures do not exceed 60° C.

Preferably, a multi-effect evaporator is used, so that temperatures can be lowered as the liquid passes through the evaporator, ensuring that the more concentrated material is not exposed to temperatures >40° C., whereas the more dilute material can tolerate temperatures of up to 60° C.

Using evaporation, the water-soluble extract can be concentrated up to 70% solids, e.g. to 20% solids, or to 50% solids, or to 65% solids. In a most preferred embodiment the final extract comprises 60-62% solids after concentration according to step (d).

The effect of temperature can be quantified by measuring the browning index. Temperatures should be sufficiently low such that the final concentrated product should not exceed 0.8 AU.

The final concentrate formed following steps (a), (b), (c) and utilising an evaporator according to step (d) preferably has a browning index of <0.8 AU, a pH of 4.0-4.3 and a density of 1.15-1.20.

Concentration Using Membrane Processes

Alternatively Membrane processes which allow water to pass through the membrane while retaining all other components within the membrane can also be used. Examples of specific techniques are reverse osmosis, or nanofiltration. Both can be used to concentrate the water-soluble extract to the required degree, while operating at low temperatures (<40° C.).

Drying Techniques

Drying technologies can also be used to remove water from the water-soluble extract. Suitable drying techniques include spray drying, with or without carrier materials (e.g. potato starch, tapioca starch, maltodextrins); vacuum drum drying, with or without carrier materials; or roller drying, with or without carrier materials.

Preparation of Low Sugar Fruit Extracts

The methods described above were designed for the production of a concentrate containing all the elements originally present in the water-soluble extract.

In a preferred embodiment of the invention the method of the first aspect of the invention may be adapted to result in a concentrate that is enriched (e.g. 25-35 times) in the bioactive components.

Enrichment of the bioactive components within the water-soluble extract can be achieved by removing the soluble sugars which form the largest portion of its dry matter content.

Low sugar fruit extracts may be prepared by following steps (a), (b) and (c) above and then employing a further step in the methods before the final concentration step ((d) above)

Removal of the soluble sugars can be achieved by:
(1) precipitation, e.g. by adding ethanol to the solution to a final concentration of 90%, which will result in precipitation of free glucose, fructose and sucrose;
(2) Partial removal of free sugars by digestion, by enzymes (e.g. glucose oxidase);
(3) by microbial (bacteria or yeast) treatment; or
(4) removing free sugars from the water-soluble extract by resin-mediated separation of the extract components It is preferred that free sugars are removed from the water-soluble extract by resin-mediated separation of the extract components ((4) above). The inventors have developed a method in which a food grade resin (Amberlite FPX66) is employed to adsorb all the extract components, with the exception of free sugars, organic acids, and salts. These are not adsorbed by the resin and may be discarded after passing through. The extract components adsorbed onto the resin, which comprise amino acids, bioactive components, and products of browning reactions (Maillard degradation products), are then recovered from the resin by elution with ethanol/water mixtures, e.g. 50% ethanol, or 80% ethanol. Ethanol may be removed from the resulting solution by evaporation under reduced pressure (e.g. in an explosion-proof conventional evaporator, or in a Centritherm centrifugal concentrator), or by reverse osmosis.

After the removal of the sugars the concentration of the product may be adjusted employing the procedures discussed in step (d) above.

The resulting low sugar extract is preferably a concentrated aqueous solution containing <1% sugar, and containing >95% of the bioactive components contained in the start mix.

Fruit Extracts

The extracts prepared according to the methods of the first aspect of the invention represent novel fruit extracts with surprising efficacy for preventing platelet aggregation.

Therefore according to a second aspect of the invention there is provided a fruit extract capable of inhibiting platelet aggregation prepared according to the methods of the first aspect of the invention.

Extracts according to the second aspect of the invention may be used to treat, and in particular prevent the development, of disease states that are characterised by inappropriate platelet aggregation. The inventors have established that the extracts of the invention are particularly useful for:

(a) preventing or reducing the occurrence of a hypercoagulable or prothrombotic state, such as is often associated with conditions such as diabetes mellitus, inflammatory bowel disease, hyperlipidaemia (b) preventing or reducing the development of atherosclerosis (c) preventing the development of coronary disease (e.g. myocardial infarctions and stroke and in preventing further thrombo-embolic events in patients who have suffered myocardial infarction, stroke or unstable angina).

(d) preventing the development of restenosis following angioplasty and bypass procedures.

(e) treating coronary disease resulting from thromboembolic disorders such as myocardial infarction in conjunction with thrombolytic therapy.

(f) preventing or reducing the risk of deep vein thrombosis (g) benefiting the circulation to maintain good circulatory health (h) maintaining healthy blood flow in the cardiovascular system.

It will be appreciated that extracts of the invention will have general health benefits for maintaining cardiovascular and heart health by reducing platelet aggregation, benefiting the circulation, and/or normalizing or otherwise benefitting blood flow (e.g. as outlined in (g) and (h) above).

Indeed so advantageous are these uses of the extracts, that the invention further provides a fruit extract prepared according to the methods of the invention for use as a medicament for normalizing or otherwise benefiting blood flow in a patient. The invention also provides a fruit extract comprising a glycosylated phenolic acid or a phenolic ester, or derivatives thereof; a glycosylated flavonoid; and a nucleoside for use as a medicament for normalizing or otherwise benefiting blood flow in a patient.

Compositions comprising extracts of the invention will be useful as pharmaceutical products but will also represent beneficial functional foods or "nutraceuticals". Accordingly preferred uses of the compositions are as medicaments and functional foods or drinks (as outlined below).

Preferred fruit extracts of the invention are aqueous extracts from ripe, (i.e. red) tomatoes, and are water soluble.

The term "water soluble" as used herein means that the tomato extracts are soluble at room temperature, e.g. at 25° C. The extracts have also been found to be water soluble at much lower temperatures, for example at temperatures as low as 4° C.

The extracts contain no, or negligible concentrations of, lycopene. For example, the extracts contain less than 0.5% by weight (dry weight) of lycopene, e.g. less than 0.1%, or less than 0.05%, or less than 0.01%, or less than 0.005%, or less than 0.001%, or less than 0.0005%, or less than 0.0001%, by weight (dry weight) of lycopene.

The extracts are substantially free from water-insoluble particulate material. Thus, for example, they contain less than 0.5% by weight (dry weight) of water-insoluble particulate material, e.g. less than 0.1%, or less than 0.05%, or less than 0.01%, or less than 0.005%, or less than 0.001%, or less than 0.0005%, or less than 0.0001%, by weight (dry weight) of water-insoluble particulate material. In one embodiment, the extracts contain no water-insoluble particulate material.

The term "active fraction" as used herein refers to a fraction isolated from a tomato extract, which fraction has the ability to reduce platelet aggregation.

The inventors research (See Example 1) established that fruit extracts may be prepared in which a number of bioactives are enriched or maintained in an extract that is subsequently to be used to prevent or treat medical conditions characterised by inappropriate platelet aggregation. The methods of the first aspect of the invention were developed in order to maintain such bioactives. The inventors have established that extracts prepared according to invention comprise a number of bioactive molecules including:

(A) Bioactive Phenolic Compounds in the Extract of the Invention

The inventors have established that a number of molecules based on phenol and derivatives thereof are contained within fruit and have efficacy for preventing platelet aggregation (see Example 1).

In particular cinnamic acid, and derivatives thereof, were found to be particularly effective for inhibiting platelet aggregation. Therefore the methods of the first aspect of the invention were designed to ensure the extract comprises cinnamic acid or a derivative thereof as defined by formula I:

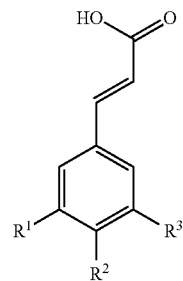

Formula I

In formula I, R1 and R2 and R3 may be independently selected from H, OH and Ome.

The compound may be Cinnamic acid per se (where R1, R2 and R3 of formula I are H) or may be any one of a number of derivatives, including:

4-Hydroxycinnamic acid (p-Coumaric acid)

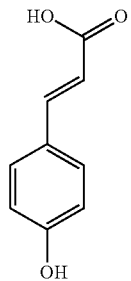 [SMILES: O=C(O)/C=C/c1ccc(O)cc1]

3,4-Dihydroxycinnamic acid (Caffeic acid)

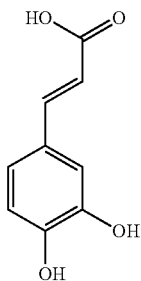 [SMILES: O=C(O)/C=C/c1ccc(O)c(O)c1]

4-Hydroxy-3-methoxycinnamic acid (Ferulic acid)

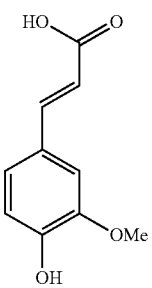 [SMILES: COc1cc(/C=C/C(=O)O)ccc1O]

4-Hydroxy-3,5-dimethoxycinnamic acid (Sinapic acid)

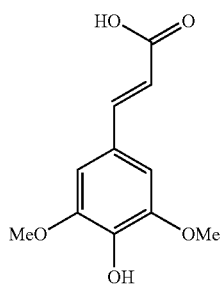 [SMILES: COc1cc(/C=C/C(=O)O)cc(OC)c1O]

The inventors also identified a further class of plant phenol derivatives, benzoic acids and derivatives thereof, in fruit extracts that are also effective for inhibiting platelet aggregation. Therefore, the methods of the first aspect of the invention may be adjusted to ensure that the extract comprises a benzoic acid or derivative thereof as define by formula II:

Formula II

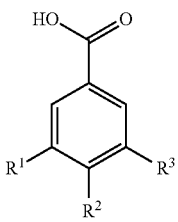

In formula II, R1 and R2 and R3 are as previously defined.

Accordingly preferred extracts according to the second aspect of the invention may comprise Benzoic acid per se (wherein each of R1, R2 and R3 are H) or any one of a number of derivatives, for example:

4-Hydroxybenzoic acid (p-Hydroxybenzoic acid)

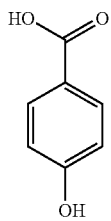

3,4-Dihydroxybenzoic acid (Protocatechuic acid),

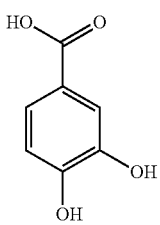

3,4,5-Trihydroxybenzoic acid (Gallic Acid)

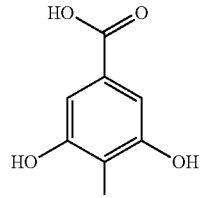

4-Hydroxy-3,-methoxybenzoic acid (Vanillic acid)

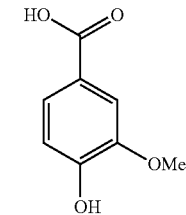 [SMILES: COc1cc(C(=O)O)ccc1O]

4-Hydroxy-3,5-dimethoxybenzoic acid (syringic acid)

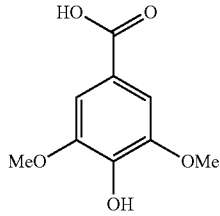 [SMILES: COc1cc(C(=O)O)cc(OC)c1O]

During the inventors work with fruit extracts they were surprised to discover that phenolic bioactives that are conjugated with other molecules either via an ester linkage at the carboxylic acid group, to form a carboxylic ester, or via an ether linkage at a phenolic hydroxyl substituent, to form a glycoside, were particularly efficacious for reducing platelet aggregation and therefore useful for treating or preventing the development of a variety of cardiovascular conditions. Therefore, the method of the first aspect of the invention was designed to ensure that the extract comprised a phenolic bioactive conjugated with other molecules.

It is preferred that the bioactives are conjugated to sugars to form glycosides. The inventors have found that a number of different bioactive glycosides are contained within the extracts. Accordingly, by the term "glycoside", we mean at least one hexose or pentose sugar residue conjugated to the bioactive; preferably 1-5 and more preferably 1-3 monosaccharide units are added by reaction at an OH group on the bioactive compound. Glucose, galactose or arabinose and also di-/tri-saccharides of these sugars are most preferably added to the compound to form phenolic acid derivative glycosides.

Alternatively the bioactive compounds may be conjugated to a number of compounds found in plants (e.g. tartaric acid, quinic acid) to form esters. Such compounds may be open chain compounds such as tartaric acid, or heterocyclic compounds such as quinic acid and may be derived from the carbohydrate pathway in plants. Tartaric acid or quinic acid are most preferably added to the compound to form phenolic ester derivatives.

It is preferred that method of the invention enriches the extract such that it comprises a glycoside selected from the group comprising: Caffeic acid 3-O-glycoside, Caffeic acid 4-O-glycoside, Ferulic acid 4-O-glycoside, p-Coumaric acid 4-O-glycoside, or an esterified derivative selected from the group comprising Caffeoylquinic acids (e.g. 3-O-Caffeoylquinic acid, 4-O-Caffeoylquinic acid or 5-O-Caffeoylquinic acid), Feruloylquinic acids, p-Coumaroylquinic acids, Caffeoyltartaric acids, Feruloyltartaric acids, p-Coumaroyltartaric acids, dimers of quinic acid derivatives.

Accordingly the extract of the second aspect of the invention may comprise at least one glycoside of Cinnamic acid or derivative thereof selected from the compounds listed above and may also comprise at least one glycoside of a Benzoic acid or derivative thereof selected from the compounds listed above.

(B) Bioactive Flavonoid Compounds in the Extract of the Invention

The inventors also established that optimal inhibition of platelet aggregation is achieved in extracts that also contain a flavonoid, or derivatives thereof.

The extract preferably contains a flavonoid of general formula (III):

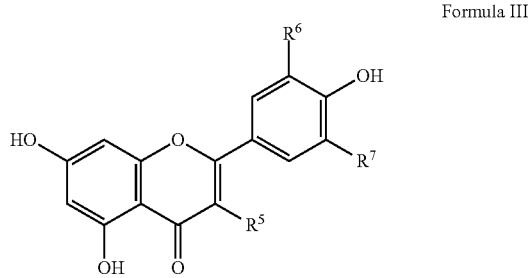

Formula III wherein R5, R6 and R7 are independently H, OH.

Preferably the extract comprises one of the following flavonoids:

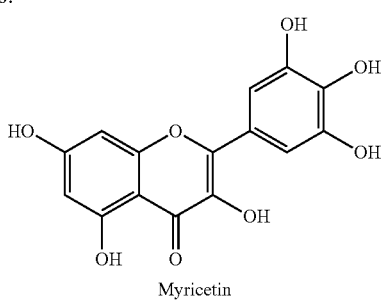

Myricetin

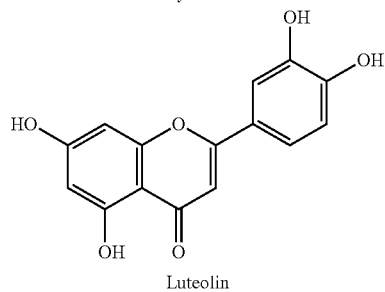

Luteolin

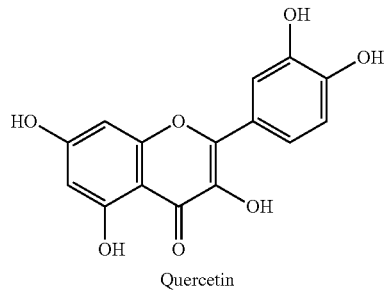

Quercetin

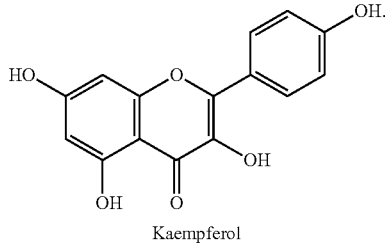

Kaempferol

It is most preferred that the extract contains Quercetin or Kaempferol or derivatives thereof.

The inventors have also established that bioactive flavonoids that are conjugated with other molecules are particularly efficacious for reducing platelet aggregation. Therefore, in a most preferred embodiment of the invention, the extract comprises flavonoid compounds conjugated as defined above (i.e. to sugars, tartaric acid, quinic acid and the like).

Naringenin and derivatives thereof represent another type of flavonoid found in extracts according to the second aspect of the invention which the inventors have found have activity for inhibiting platelet aggregation. Therefore the extract may comprise molecules of general formula IV.

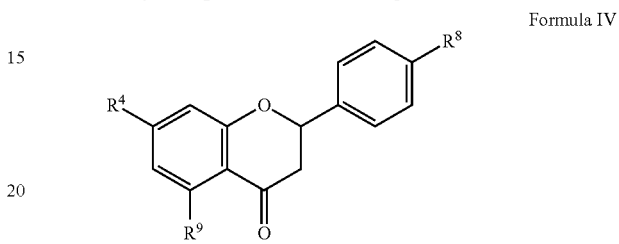

Formula IV

R4, R8 and R9 are as previously defined.

A preferred compound defined by Formula IV, contained within the extract, is Naringenin.

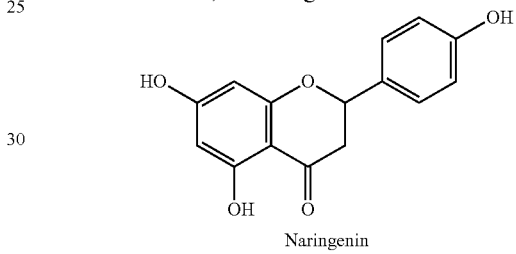

Naringenin

The inventors have also established that the compounds of General formula (IV) that are conjugated with other molecules are particularly efficacious for reducing platelet aggregation. Therefore, in a most preferred embodiment of the invention, the extract comprises flavonoid compounds conjugated as defined above (i.e. to sugars, tartaric acid, quinic acid and the like A most preferred glycoslyated flavonoid compound found in the extracts of the invention is Naringin.

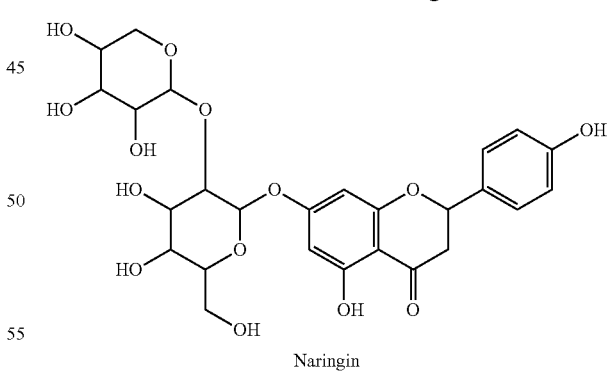

Naringin

The inventors have found that preferred extracts may comprise phenolic and flavonoid bioactive compounds discussed above that are conjugated with each other. For example, Caffeic acid 4-O-Rutinoside is a molecule with anti-platelet aggregation properties where a glycoside link is made between Caffeic acid and a sugar residue on Rutin (which comprise Quercetin).

(C) Nucleosides/Nucleotides

As contemplated in WO 99/55350, fruit extracts with anti-platelet activity may further comprise a nucleoside. The extract may comprise at least one nucleoside selected from Adenosine 5'-monophosphate, Cytidine, Uridine, Adenosine, Inosine, Guanosine and Guanosine 5'-monophosphate.

It will be appreciated that the inventors have identified a number of bioactive compounds in different fractions of tomato extracts. They were then able to adapt methods for preparing fruit abstracts such that the active compounds they identified were maintained and/or enriched in such fruit extracts.

According to a third aspect of the invention there is provide a fruit extract comprising:
(a) glycosylated phenolic acid or a phenolic ester, or derivatives thereof;
(b) a glycosylated flavonoid; and
(c) a nucleoside.

(a) The glycosylated phenolic acid is preferably a glycosylated cinnamic acid or derivative thereof. The extract most preferably comprises at least one of Caffeoyl-4-O-quinic acid, Caffeoyl-4-O-glucoside, Coumaroyl-4-O-glycoside (gluc/gal) or Coumaroyl-4-O-glycoside (disaccharide). The extract may comprise 1, 2, 3 or each of these glycosides. In a preferred embodiment of the invention, the fruit extract according to the third aspect of the invention comprises a glycosylated cinnamic acid or derivative thereof and a benzoic acid or derivate thereof as discussed above.

It is most preferred that the extract comprise Caffeic acid glucoside; and/or p-Coumaric acid hexose/dihydrokaempferol hexose; and/or Ferulic acid glycoside; and/or a p-Coumaric acid derivative (b) The glycosylated flavonoid is preferably Naringin, Quercetin-3-O-glucoside or Rutin. The extract may comprise one, two or each of these glycosides. The bioactive is most preferably Rutin.

(c) The nucleoside may be any one of AMP, Uridine, Adenosine, Guanosine or GMP. The extract may comprise 1, 2, 3, 4 or each of these nucleosides. The nucleoside is preferably Guanosine and/or Adenosine 3'-mono phosphate The fruit extract according to the third aspect of the invention may also optionally contain a steroidal glycoside such as Tomatidine.

The fruit extracts preferably contains no fats or carotenoids.

Two preferred extracts, which may be prepared from fruits and particularly tomato according to the methods of the invention, were found to comprise the following bioactive compounds in the specified concentrations (mg/g):

(1) A preferred extract, prepared according to the methods described in Example 2, comprises:
(a) The following Glycosylated phenolic acid or phenolic esters:
Caffeic acid glucoside (0.01-1 mg/g);
p-Coumaric acid hexose/dihydrokaempferol hexose mixture (0.05-2.5 mg/g)
Ferulic acid glycoside (0.025-5 mg/g); and
p-Coumaric acid derivative (0.01-1 mg/g).
(b) The glycosylated flavonoid: Rutin (0.01-1 mg/g).
(c) The following nucleosides/nucleotides:
Guanosine (0.1-5 mg/ml); and
Adenosine 3'-monophosphate (0.5-25 mg/ml)

(2) A preferred low sugar extract, prepared according to the methods described in Example 3, comprises:
(a) The following Glycosylated phenolic acid or phenolic esters:
Caffeic acid glucoside (1-25 mg/g);
p-Coumaric acid hexose/dihydrokaempferol hexose mixture (5-100 mg/g);
Ferulic acid glycoside (25-300 mg/g); and
p-Coumaric acid derivative (1-25 mg/g)
(b) the glycosylated flavonoid: Rutin (1-25 mg/g)
(c) the following nucleosides/nucleotides:
Guanosine (1-50 mg/g); and
Adenosine 3'-mono phosphate (1-50 mg/g);

Two specific tomato extracts embodying the second or third aspects of the invention are identified in table 1. Table 1 identifies 16 compounds (in column 3 and ID No. is also provided in column 2) that were isolated and assayed (see Example 1) and found to have most anti-platelet activity. Accordingly it is preferred that extracts according to the second or third aspects of the invention comprise each of these 16 bioactive compounds. It will be appreciated that the methods of the first aspect of the invention are preferably designed to optimise the activity of these compounds in a fruit extract.

Table 1 also identifies the ranges (mg/g wet weight) of each bioactive compound found in extracts prepared according to the methods specified in Examples 2 and 3 respectively. The average concentration (mg/g) is also shown. Most preferred extracts according to the second or third aspects of the invention comprise bioactive compounds in these specified ranges.

TABLE 1 antiplatelet compounds in tomato extract, grouped by compound type.

| Type of bioactive | Compound ID | Bioactive Compound | Preferred Extract prepared according to methods of Example 2 | | | Preferred Low Sugar Extract prepared according to methods of Example 3 | | |
|---|---|---|---|---|---|---|---|---|
| | | | lower range mg/g | upper range mg/g | average mg/g | lower range mg/g | upper range mg/g | average mg/g |
| Nucleotides | 2 | Adenosine | 0.382 | 2.440 | 2.033 | 1.800 | 2.927 | 2.439 |
| | 4 | Guanosine | 0.400 | 1.759 | 1.466 | 6.970 | 19.354 | 16.128 |
| | 5 | Adenosine 3'-monophospate | 1.312 | 11.491 | 9.576 | 6.421 | 16.087 | 13.406 |
| | 6 | Adenosine 5'-monophospate | | | | | | |
| Phenolic glycosides | 8 | p-Coumaric acid hexose/quinic acid derivative | 0.050 | 0.456 | 0.380 | 9.418 | 11.867 | 9.889 |
| | 9 | Caffeic acid glucoside | 0.069 | 0.477 | 0.398 | 3.736 | 13.402 | 11.168 |
| | 10 | Ferulic acid hexose | 0.028 | 0.048 | 0.040 | 0.706 | 1.340 | 1.117 |
| | 11 | p-Coumaric acid hexose/ dihydrokaempferol hexose mixture | 0.277 | 0.997 | 0.831 | 26.121 | 40.288 | 33.573 |

TABLE 1-continued antiplatelet compounds in tomato extract, grouped by compound type.

| Type of bioactive | Compound ID | Bioactive Compound | Preferred Extract prepared according to methods of Example 2 | | | Preferred Low Sugar Extract prepared according to methods of Example 3 | | |
|---|---|---|---|---|---|---|---|---|
| | | | lower range mg/g | upper range mg/g | average mg/g | lower range mg/g | upper range mg/g | average mg/g |
| | 12 | p-Coumaric acid/caffeic acid conjugate, glycosylated | 0.170 | 1.419 | 1.182 | 90.872 | 131.722 | 109.768 |
| | 13 | Ferulic acid glycoside | 0.155 | 1.199 | 0.999 | 85.333 | 199.679 | 166.399 |
| | 14 | Chlorogenic acid | 0.131 | 0.953 | 0.794 | 18.274 | 43.366 | 36.138 |
| Phenolic ester derivatives | 15 | p-Coumaric acid derivative | 0.105 | 0.332 | 0.277 | 8.620 | 16.584 | 13.820 |
| Flavonoid glycosides | 23 | Quercetin-3-O-glycoside | 0.050 | 0.324 | 0.270 | 8.463 | 13.257 | 11.048 |
| | 25 | Quercetin-3-O-trisaccharides | 0.157 | 0.610 | 0.508 | 14.679 | 24.799 | 20.666 |
| | 26 | Naringin | 0.739 | 2.103 | 1.753 | 38.016 | 61.709 | 51.424 |
| | 27 | Rutin | 0.583 | 2.804 | 2.337 | 50.688 | 106.147 | 88.456 |

Following detailed analysis of bioactive compounds contained within a tomato extract the inventors came to the conclusion that a further 16 compounds also had anti-aggregation activity. It was therefore realised that most preferred extracts according the second or third aspects of the invention contain the 32 bioactive compounds identified in Table 2.

TABLE 2

Most preferred extracts comprising 32 bioactive compounds

| Group | Compound ID | Bioactive Compound | Preferred Extract prepared according to methods of Example 2 | | | Preferred Low Sugar Extract prepared according to methods of Example 3 | | |
|---|---|---|---|---|---|---|---|---|
| | | | lower range mg/g | upper range mg/g | average mg/g | lower range mg/g | upper range mg/g | average mg/g |
| Nucleosides | 1 | Cytidine | 0.487 | 2.051 | 1.709 | 21.971 | 36.911 | 30.759 |
| | 2 | Adenosine | 0.382 | 2.440 | 2.033 | 1.800 | 2.927 | 2.439 |
| | 3 | Uridine | 0.414 | 2.089 | 1.741 | 21.917 | 31.340 | 26.117 |
| | 4 | Guanosine | 0.400 | 1.759 | 1.466 | 6.970 | 19.354 | 16.128 |
| Nucleotides | 5 | Adenosine 3'-monophosphate | 1.312 | 11.491 | 9.576 | 6.421 | 16.087 | 13.406 |
| | 6 | Adenosine 5'-monophosphate | | | | | | |
| Phenolic acid glycosides | 7 | Mixed phenolic acid glycosides | 0.352 | 0.956 | 0.796 | 20.982 | 145.537 | 121.281 |
| | 8 | p-Coumaric acid hexose/quinic acid derivative | 0.050 | 0.456 | 0.380 | 9.418 | 11.867 | 9.889 |
| | 9 | Caffeic acid glucoside | 0.069 | 0.477 | 0.398 | 3.736 | 13.402 | 11.168 |
| | 10 | Ferulic acid hexose | 0.028 | 0.048 | 0.040 | 0.706 | 1.340 | 1.117 |
| | 11 | p-Coumaric acid hexose/dihydrokaempferol hexose mixture | 0.277 | 0.997 | 0.831 | 26.121 | 40.288 | 33.573 |
| | 12 | p-Coumaric acid/caffeic acid conjugate, glycosylated | 0.170 | 1.419 | 1.182 | 90.872 | 131.722 | 109.768 |
| | 13 | Ferulic acid glycoside | 0.155 | 1.199 | 0.999 | 85.333 | 199.679 | 166.399 |
| | 14 | Chlorogenic acid | 0.131 | 0.953 | 0.794 | 18.274 | 43.366 | 36.138 |

TABLE 2-continued

Most preferred extracts comprising 32 bioactive compounds

| Group | Compound ID | Bioactive Compound | Preferred Extract prepared according to methods of Example 2 | | | Preferred Low Sugar Extract prepared according to methods of Example 3 | | |
|---|---|---|---|---|---|---|---|---|
| | | | lower range mg/g | upper range mg/g | average mg/g | lower range mg/g | upper range mg/g | average mg/g |
| Phenolic ester derivatives | 15 | p-Coumaric acid derivative | 0.105 | 0.332 | 0.277 | 8.620 | 16.584 | 13.820 |
| | 16 | Caffeoyl-quinic acid dimer #1 | 0.066 | 0.701 | 0.584 | 13.850 | 85.176 | 70.980 |
| | 17 | Caffeoyl-quinic acid dimer #2 | 0.142 | 0.701 | 0.584 | 12.672 | 22.731 | 18.943 |
| Phenolic acids | 18 | Caffeic acid | 0.058 | 0.873 | 0.727 | 5.842 | 9.042 | 7.535 |
| | 19 | p-coumaric acid | 0.046 | 0.488 | 0.407 | 11.403 | 27.568 | 22.974 |
| | 20 | Benzoic acid | 0.006 | 0.077 | 0.064 | 0.959 | 1.554 | 1.295 |
| | 21 | Ferulic acid | 0.016 | 0.140 | 0.117 | 0.584 | 1.113 | 0.927 |
| | 22 | Cinnamic acid | 0.028 | 0.084 | 0.070 | 1.966 | 6.896 | 5.747 |
| Flavonoid glycosides | 23 | Quercetin-3-O-glycoside | 0.050 | 0.324 | 0.270 | 8.463 | 13.257 | 11.048 |
| | 24 | Kaempferol glycoside | 0.008 | 0.049 | 0.041 | 1.269 | 5.277 | 4.398 |
| | 25 | Quercetin-3-O-trisaccharides | 0.157 | 0.610 | 0.508 | 14.679 | 24.799 | 20.666 |
| | 26 | Naringin | 0.739 | 2.103 | 1.753 | 38.016 | 61.709 | 51.424 |
| | 27 | Rutin | 0.583 | 2.804 | 2.337 | 50.688 | 106.147 | 88.456 |
| Flavonoid ester derivatives | 28 | Flavonoid conjugate | 0.004 | 0.032 | 0.027 | 0.846 | 1.733 | 1.444 |
| | 29 | Trace flavonoids + glycosides | 1.253 | 3.900 | 3.250 | 90.660 | 319.469 | 266.224 |
| Flavonoids | 30 | Quercetin | 0.014 | 0.130 | 0.108 | 3.787 | 20.578 | 17.149 |
| | 31 | Kaempferol | 0.039 | 0.180 | 0.150 | 3.749 | 8.230 | 6.858 |
| | 32 | Naringenin | trace | 1.540 | trace | trace | 25.600 | trace |

A preferred extract according to the third aspect of the invention comprises the recombination of fraction 1, fraction 2 and fraction 3 as referred to in Example 1 (1.1.3) to from a recombined extract. The inventors have found that such a recombined extract is enriched in the bioactives discussed above and had a surprisingly improved efficacy for inhibiting platelet aggregation.

Pharmaceutical and Nutraceutical Formulations Comprising the Fruit Extract

The fruit extracts of the invention may be formulated for oral administration. As such, they can be formulated as solutions, suspensions, syrups, tablets, capsules, lozenges and snack bars, inserts and patches by way of example. Such formulations can be prepared in accordance with methods well known to the art.

For example, the extract may be formed into a syrup or other solution for administration orally, for example as a health drink. One or more excipients selected from sugars, vitamins, flavouring agents, colouring agents, preservatives and thickeners may be included in such syrups or solutions. Tonicity adjusting agents such as sodium chloride, or sugars, can be added to provide a solution of a particular osmotic strength, for example an isotonic solution. One or more pH-adjusting agents, such as buffering agents can also be used to adjust the pH to a particular value, and preferably maintain it at that value. Examples of buffering agents include sodium citrate/citric acid buffers and phosphate buffers.

Alternatively, the extract may be dried (e.g. by spray drying or freeze drying) and the dried product formulated in a solid or semi solid dosage form, for example as a tablet, lozenge, capsule, powder, granulate or gel.

Compositions containing the extracts can be prepared without any additional components. Alternatively, they may be prepared by adsorbing on to a solid support; for example a sugar such as sucrose, lactose, glucose, fructose, mannose or a sugar alcohol such as xylitol, sorbitol or mannitol; or a cellulose derivative. Other particularly useful adsorbents include starch-based adsorbents such as cereal flours for example wheat flour and corn flour.

For tablet formation, the extract may typically be mixed with a diluent such as a sugar, e.g. sucrose and lactose, and sugar alcohols such as xylitol, sorbitol and mannitol; or modified cellulose or cellulose derivative such as powdered cellulose or microcrystalline cellulose or carboxymethyl cellulose. The tablets will also typically contain one or more excipients selected from granulating agents, binders, lubricants and disintegrating agents. Examples of disintegrants include starch and starch derivatives, and other swellable polymers, for example crosslinked polymeric disintegrants such as cross-linked carboxymethylcellulose, crosslinked polyvinylpyrrolidone and starch glycolates. Examples of lubricants include stearates such as magnesium stearate and stearic acid. Examples of binders and granulating agents include polyvinylpyrrolidone. Where the diluent is not naturally very sweet, a sweetener can be added, for example ammonium glycyrrhizinate or an artificial sweetener such as aspartame, or sodium saccharinate.

The extracts can also be formulated as powders, granules or semisolids for incorporation into capsules. When used in the form of powders, the extracts can be formulated together with any one or more of the excipients defined above in relation to tablets, or can be presented in an undiluted form. For presentation in the form of a semisolid, the dried extracts can be dissolved or suspended in a viscous liquid or semi-solid vehicle such as a polyethylene glycol, or a liquid carrier such as a glycol, e.g. propylene glycol, or glycerol or a vegetable or fish oil, for example an oil selected from olive oil, sunflower oil, safflower oil, evening primrose oil, soya oil, cod liver oil, herring oil, etc. Such extracts can be filled into capsules of either the hard gelatine or soft gelatine type or made from hard or soft gelatine equivalents, soft gelatine or gelatine-equivalent capsules being preferred for viscous liquid or semisolid fillings.

Extracts according to the invention can also be provided in a powder form for incorporation in to snack food bars for example fruit bars, nut bars, and cereal bars. For presentation in the form of snack food bars, the extracts can be admixed with any one or more ingredients selected from dried fruits such as sun-dried tomatoes, raisins and sultanas, groundnuts or cereals such as oats and wheat.

Extracts according to the invention may also be provided in a powder form for reconstitution as a solution. As such they can also contain soluble excipients such as sugars, buffering agents such as citrate and phosphate buffers, and effervescent agents formed from carbonates, e.g. bicarbonates such as sodium or ammonium bicarbonate, and a solid acid, for example citric acid or an acid citrate salt.

In one preferred embodiment, an extract according to the invention is provided in powder form optionally together with a preferred solid (e.g. powdered) excipient for incorporation into capsules, for example a hard gelatine capsule.

A solid or semisolid dosage form of the present invention can contain up to about 1000 mg of the composition, for example up to about 800 mg.

The extract can be presented as food supplements or food additives, or can be incorporated into foods, for example functional foods or nutraceuticals.

The extracts of the invention can be presented in the form of unit dosage forms containing a defined concentration of compounds with activity for inhibiting platelet aggregation. Such unit dosage forms can be selected so as to achieve a desired level of biological activity. For example, a unit dosage form can contain an amount of up to 1000 mg (dry weight) of a composition according to the present invention, more typically up to 800 mg, for example 50 mg to 800 mg, e.g. 100 mg to 500 mg. Particular amounts of the composition that may be included in a unit dosage form may be selected from 50 mg, 100 mg, 150 mg, 200 mg, 250 mg, 300 mg, 350 mg, 400 mg, 450 mg, 550 mg, 600 mg, 650 mg, 700 mg, 750 mg and 800 mg.

The extracts of the invention can be included in a container, pack or dispenser together with instructions for administration.

Preferred products comprising extracts according to the invention are defined in Example 5.

Dosing

For the treatment of the diseases and conditions concerned, the quantity of the extract according to the invention administered to a patient per day will depend upon the particular condition or disease under treatment and its severity, and ultimately it will be at the discretion of the physician. The amount administered however will typically be a non-toxic amount effective to treat the condition in question.

For a composition which contains sugars, the recommended daily dose of a fruit extract prepared according to the methods of the invention is between 0.5 g and 20 g and more preferably between 2 g and 7 g. A daily dose may be about 3 g. For a low-sugar composition (see above), the recommended daily dose may be between 10 mg and 500 mg and is more preferably between about 85 mg and about 150 mg.

A typical daily dosage regime for a human patient suffering from a cardiovascular disease may be from about 70 mg to 285 mg, preferably about 25 mg to 100 mg per kilogram body weight of an extract containing fruit sugars and may be from about 1 mg to 2.25 mg 100 mg per kilogram body weight of a low-sugar extract.

The extract can be administered in single or multiple dosage units per day, for example from one to four times daily, preferably one or two times daily. It is most preferred that the extract is given as a single daily dose.

The extracts can be administered in the form of tomato juice or concentrates thereof alone or in admixture with other fruit juices such as orange juice.

Indications of Therapeutic Effectiveness

The ability of compositions comprising extracts of the invention to provide beneficial therapeutic effects may be assessed with reference to a number of different parameters. The Examples below provide details of suitable protocols for the assessment of platelet aggregation or primary haemostasis, either of which may be investigated in order to evaluate therapeutic effectiveness. The PFA-100® platelet function analyzer described in the Examples is a relatively new device for the assessment of primary haemostasis, but has been well validated (see, for instance, "The platelet-function analyzer (PFA-100®) for evaluating primary hemostasis" by M. Franchini Hematology, Volume 10, Issue 3 June 2005, pages 177-181).

Other parameters that may be assessed for this purpose include blood fluidity and blood flow, where an increase in fluidity or flow will generally be indicative of a therapeutically useful effect.

Methods of Measuring Blood Fluidity

A direct measurement of blood fluidity can be obtained using a Micro Channel Array Flow Analyser (MC-FAN), such as the MC-FAN HR300 available from Arkray, which mimics capillary vessels.

A suitable protocol for use of a MC-FAN is provide in "Determinants of the daily rhythm of blood fluidity", by Tatsushi Kimura, Tsutomu Inamizu, Kiyokazu Sekikawa, Masayuki Kakehashi and Kiyoshi Onari (*Journal of Circadian Rhythms* 2009, 7:7).

Briefly microgrooves with width 7 μm, length 30 μm, depth 4.5 1-1 m are formed, for example by photo-fabrication on the surface of a single crystal silicon chip. Suitable chip dimensions may be around 15×15 mm. The microgrooves are then formed into leak-proof microchannels that represent capillaries. This conversion into channels may, for instance, be achieved by tightly covering the channels with a cover such as an optically flat glass plate. Suitable grooves may be transformed into hermetic microchannel by soldering of an optically polished glass plate.

The dimensions of the microchannels are such that the volume of fluid which flows through one flow path is extremely small. Accordingly, it is desirable to replicate the flow channels in order to facilitate measurement of the flow rate. The reference cited above describes the production of a device in which 8736 flow paths of the same size are created. The silicon substrate may then be mounted onto the microchannel flow system, MC-FAN (Hitachi Haramachi Electronics Co., Ltd, Ibaragi, Japan), which makes it possible to directly observe the flow of blood cell elements through the microchannel under a microscope connected to an image display unit. Flow can be continuously viewed while the passage time for a given volume of blood is determined automatically.

A suitable value of blood passage may be expressed as a function of the actual whole blood passage time over saline solution passage time of 12 seconds at a pressure of 20 em H20, as follows:

$$\text{Blood passage time (revised value; sec)} = \frac{\text{Whole blood passage time (actual value)}}{\text{Saline solution passage time}} \times 12$$

Methods of Measuring Blood Flow

Doppler ultrasound flowmetry is a widely used method for assessment of blood flow through intact blood vessels in vivo. Suitable methods using Doppler ultrasound are well known to those skilled in the art, and include those described in "Measurement of blood flow by ultrasound: accuracy and sources of error." By R. W. Gill (Ultrasound Med Bioi. 1985 July-August; 11(4):625-41).

BRIEF DESCRIPTION OF THE DRAWINGS

The invention will now be illustrated, but not limited, by the following examples, and with reference to the accompanying drawings, in which:

FIG. 7: Shows average closure times recorded at baseline (0), t=3 hours (3) after supplementation with TE or C and t=5 hours (5) after supplementation with TE or C, as described in Example 6. n=3 for each group. Significant differences between C and TE are indicated on the graph by* (P=0.011).

EXAMPLE 1

Figure 1A:
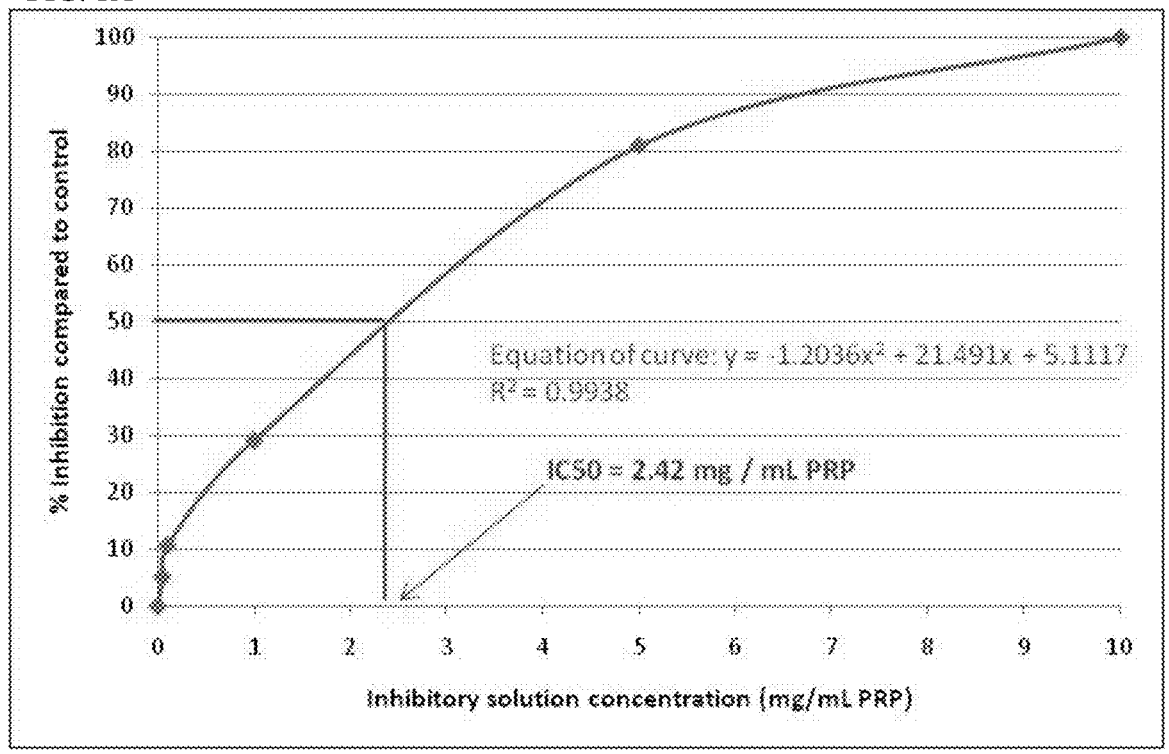
FIG. 1A-1F: represents examples of dose-response curves of % inhibition of aggregation versus inhibitor solution concentration generated for (1A) Compound 1; (1B) Compound 5; (1C) Compound 9; (1D) Compound 18; (1E) Compound 23; and (1F) Compound 30 as discussed in Example 1. (1A) and (1B) represent dose-response curves of % inhibition of ADP-mediated aggregation. (1C) and (1D) represent dose response curves of % inhibition of collagen-mediated aggregation. (1E) and (1F) represent dose-response curves of % inhibition of arachidonic acid-mediated aggregation.
Figure 1B:
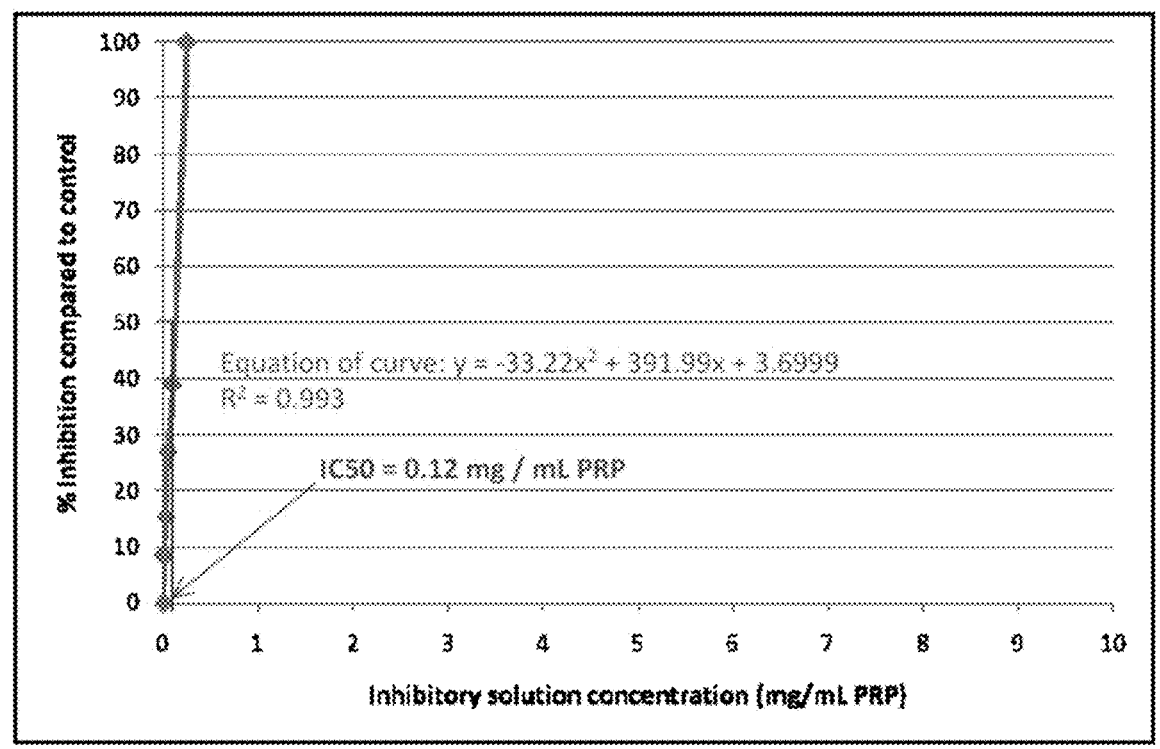
Figure 1C:
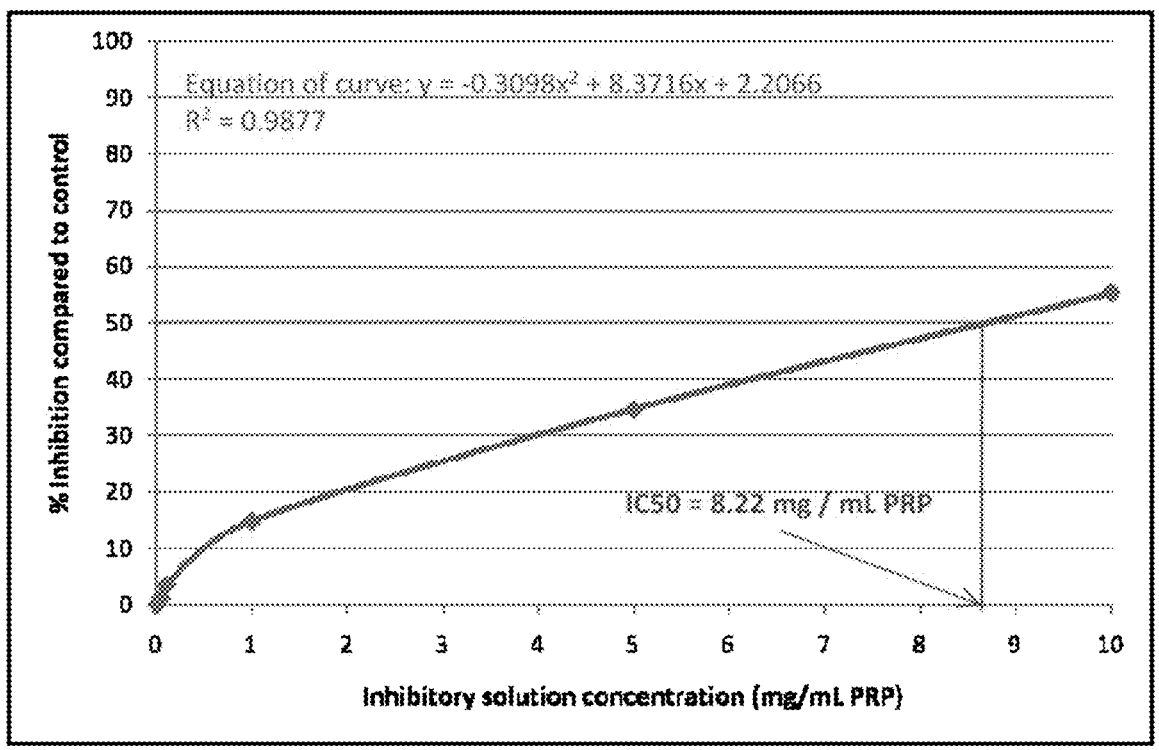
Figure 1D:
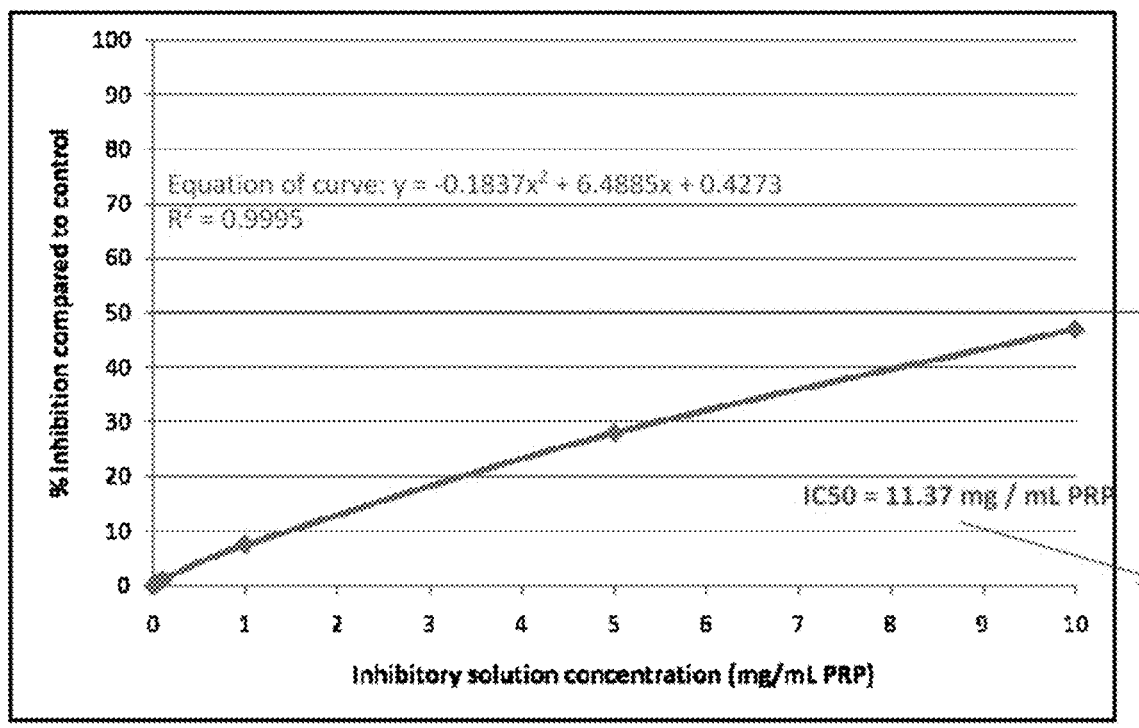
Figure 1E:
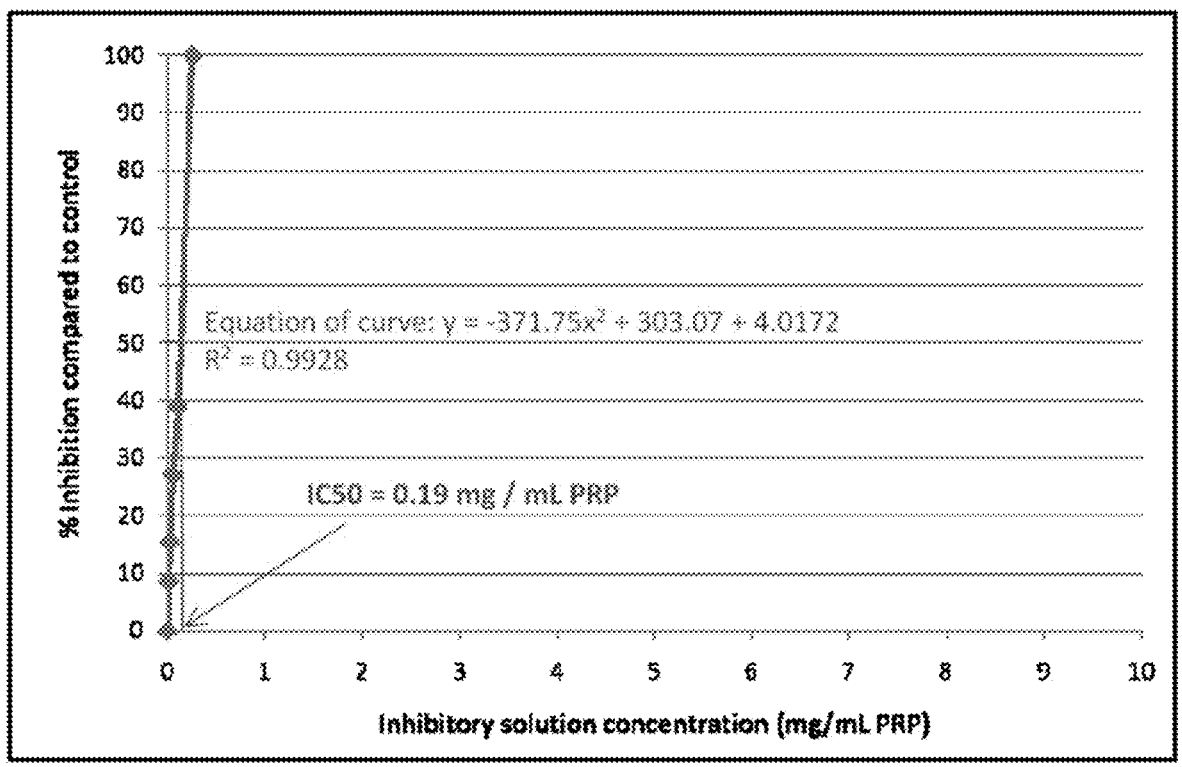
Figure 1F:
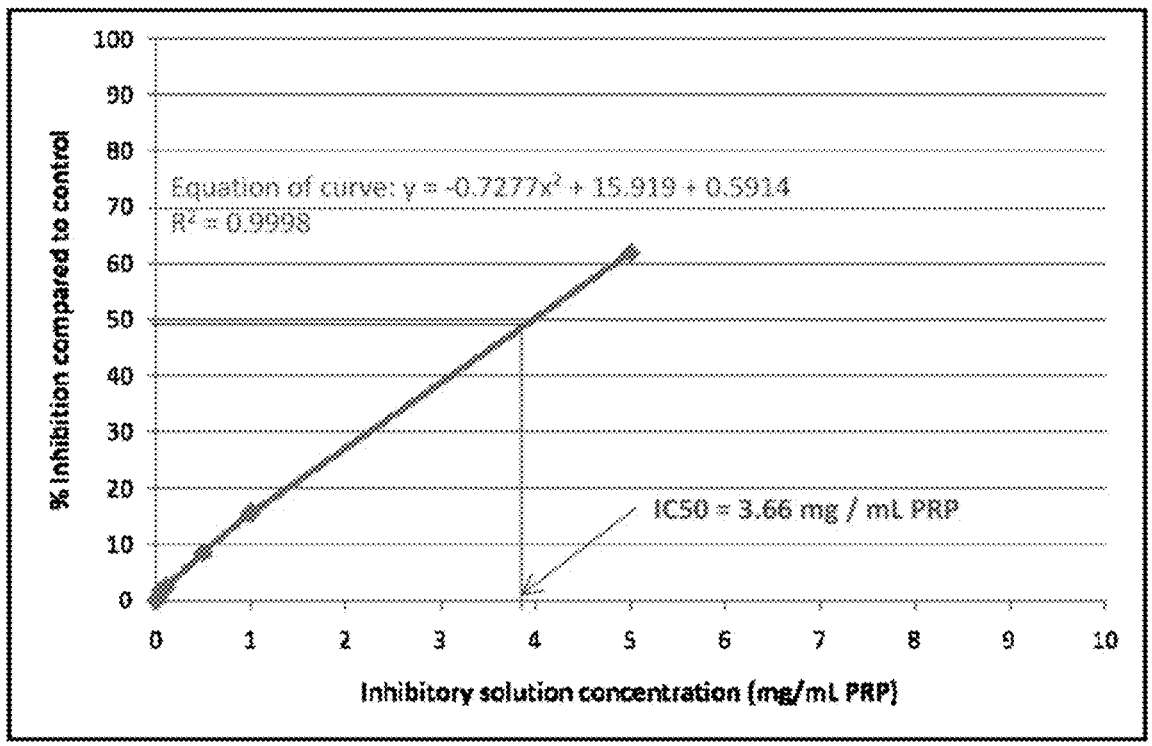

The present invention is based upon further research that was conducted in view of the antiplatelet activity identified in the fruit extract described in WO 99/55350.

The inventors conducted exhaustive experiments whereby they further fractionated tomato extracts to identify compounds within such extracts that were linked to its inhibitory effects on platelet aggregation. The inventors identified many, many compounds (not all chemically identified; and not all data presented here) with the fruit extract that had no or negligible effects on platelet aggregation. However the inventors were surprised to find that 32 compounds with notable activity feel into the classes of chemicals defined by the third aspect of the invention. This discovery led them to develop the methods of the first aspect of the invention in order that the activity of such compounds could be maintained/enriched in fruit extracts.

1.1. Methods 1.1.1 Preparation of a Tomato Extract as Defined by WO 99/55350.

A tomato extract was prepared using commercially available cold-break tomato paste of 28-30 °Brix (i.e. 28-30% solids, w/w) having a browning index (absorbance of a solution of concentration 12.5 g soluble solids/L at 420 nm)<0.350 AU as the starting material. The paste was diluted (1:5) with ultrapure water and large particulate matter was removed by centrifugal filtration followed by clarification using a Westfalia MSB-14 Separator (a centrifugal disk clarifier) at room temperature. Smaller particulate matter was then removed by microfiltration at a temperature not exceeding 45° C., to give a clear straw-coloured solution containing no insoluble spin-down solids and capable of passing through a 0.2µ filter without loss of soluble solids. This solution was concentrated by evaporation to a syrup of 65° Brix, using carefully controlled conditions and a temperature not exceeding 50° C. to limit the progress of non-enzymic browning reactions. A flash pasteurisation step (T=105° C. for 3 seconds) was incorporated at the outset of the evaporation procedure. The final product was characterised by a browning index <0.600 AU, and a microbial total plate count of <1000.

1.1.2 Enrichment of the Tomato Extract with the Active Compounds of Interest and Removal of Inactive Materials In order to yield a starting material more concentrated in bioactive components, sugars were removed from the product described above as follows.

A 130 L resin column containing FPX66 resin (Rohm and Haas) was prepared and equilibrated in ultrapure water at 4° C. The material described in 1.1.1 was diluted to approximately 8 Brix with ultrapure water, and passed through the resin column at a flow rate of approximately 260 L/minute, maintaining the temperature at 4° C. The column permeate was discarded. Once all the required material had been passed through the column, a water wash of approximately 130 L was passed through and discarded. Thereafter, the compounds which had been retained by the resin were eluted, by passing 130 L of hot water (75° C.) through the columns, followed by 130 L of 80% ethanol, followed by a further 130 L of hot water. All eluted material was retained and combined to give approximately 400 L of approximately 25% ethanolic solution containing the compounds of interest.

The dilute solution containing the compounds of interest was concentrated by reverse osmosis using Trisep ACM5 membranes at temperatures around 30° C. The ethanol/water solvent passed through this membrane, while all compounds dissolved therein remained within the membrane. Once the dilute solution had been concentrated 10-fold, i.e. volume was reduced to 40-50 L, diafiltration commenced, during which ultrapure water was added to the retentate at an equal rate to the permeate removal rate. In this way, the ethanol concentration of the solution was gradually reduced from 25% to <5%.

The ethanolic solution at ~15-20% solids was then spray-dried using an Anhydro spray-drier to form a fine, golden powder of <6% moisture content. This was the final enriched tomato extract, which was used to isolate antiplatelet components of interest.

1.1.3 Isolation and Characterisation of Individual Bioactive Compounds in the Tomato Extract A stock solution of 50 mg/mL was prepared from the dry powder described in 1.1.2, by dissolving it in ultra-pure HPLC-grade water. Semi-preparative HPLC was carried out using a Luna C18(2) 5μ semi-preparative column, 100×4.6 mm, injecting 100 μL onto the column at a time. Using a fraction collector, the UV-absorbing components contained in the tomato extract were divided into three bulk fractions. Fraction 1 contained largely nucleosides and nucleotides. Fraction 2 contained largely phenolic acid glycosides/esters, and phenolic acids. Fraction 3 contained largely flavonoid glycosides and flavonoids. The three bulk fractions were dried by freeze-drying, and redissolved in water to give solutions of 50 mg/mL. Each fraction in turn was then subjected to further semi-preparative HPLC using the same column but with different gradients, adapted to the polarity and elution characteristics of each fraction. From each bulk fraction, up to 10 individual or mixed fractions were collected using a fraction collector.

The individual fractions were freeze-dried and redissolved in 1 mL pure water. Each fraction was then examined by analytical HPLC-MS, using a Luna C18(2) 3μ analytical column, 100×4.6 mm, running an acetonitrile/formic acid gradient. Characteristics of each isolated fraction were determined by collection of its UV spectrum via a diode-array detector, and by examination of its characteristic ions generated by electrospray MS in positive ion mode.

Where necessary, final purifications (e.g. to remove minor contaminants) were carried out by further HPLC. Finally purified compounds were freeze-dried and stored frozen. Stock solutions were prepared at 50 mg/mL and diluted into HPLC buffer to produce 6 concentration levels, which were used to calibrate the HPLC method, so that response factors could be calculated for each individual compound. These calibration curves and response factors were then used to quantify the compounds present in the tomato extract. The structural types/identities of the bioactive compounds isolated are shown in Table 3.

1.1.4 Methods of Assaying Activity for Inhibiting Platelet Aggregation

The experimental protocol described below was devised to determine the 1050 values of compounds isolated as described in 1.1.3. Crude bioassays to evaluate inhibition of platelet aggregation in vitro were performed on some crude extracts (data not shown) to help select fine fractions/compounds identified by HPLC for functional activity. This approach was considered necessary to avoid the need to assay each and ever compound (the would be thousands) in the fruit extracts.

An IC50 value represents the amount of a compound, in mg, required to inhibit by 50% the platelet aggregation induced under standardised conditions in 1 mL platelet-rich plasma, in comparison with control samples.

The activity of the 32 most active compounds is given in Table 4.

Phlebotomy and Blood Samples

Blood for in vitro studies was collected from drug-free, healthy human volunteers, both male and female, aged 18-60 years, with normal platelet function. Subjects declared that they had not consumed drugs or supplements known to affect platelet function for a minimum of 10 days before providing a blood sample. Blood was collected after single venepuncture to an antecubital vein through siliconized needles into plastic citrated blood collection tubes (Sarstedt Monovettes, final concentration sodium citrate, 13 mmol/L). All blood was maintained at 37° C. from the time of blood sampling.

Preparation of Platelet-Rich Plasma

Platelet-rich plasma (PRP) was obtained by centrifugation of citrated blood for 15 minutes at 200×g, and was adjusted with platelet-poor plasma to a standard platelet number of $320\pm20\times10^9$/L prior to use. PRP was used for platelet function measurements within two hours.

Platelet Agonists

The following agonists were used for platelet function measurements. Adenosine diphosphate (ADP), final concentration 10 μmol/L; collagen, final concentration 5 mg/L; arachidonic acid, final concentration 500 U/L (all from Helena Biosciences, Sunderland, UK); thrombin receptor-activating peptide (TRAP), final concentration 25 nmol/L (Sigma-Aldrich, Poole, UK). Agonists were prepared from stock solutions immediately before use, diluting into warmed physiological saline (0.9% NaCl).

Preparation of Platelet Inhibitor Solutions

Individual platelet inhibitors were prepared at a concentration of between 500 g/L and 100 g/L in either physiological saline, ultra-pure methanol or ultra-pure DMSO (Sigma-Aldrich, Poole, UK) and stored frozen until required. Stock solutions were then diluted with physiological saline immediately prior to use.

Incubation of Platelet Inhibitors with PRP

450 μL PRP was incubated with 50 μL diluted inhibitor solution at 37° C. for 10 minutes, in low-retention epindorrfs. Inhibitor solutions were diluted such that the final concentration of methanol or DMSO in the PRP sample never exceeded 2%. Suitable control samples, containing 50 μL physiological saline matched for methanol or DMSO content as appropriate, were incubated simultaneously. For each inhibitor compound, 5 incubation concentrations were used; final concentrations of 0.05 mg/mL, 0.10 mg/mL, 1.00 mg/mL, 5.00 mg/mL and 10 mg/mL were used as standard.

Measurement of Platelet Aggregation and Inhibition of Aggregation

After incubation with platelet inhibitors, PRP samples were transferred to glass cuvettes and the extent of aggregation induced by either ADP, collagen, TRAP or arachidonic acid was monitored over 10 minutes on a platelet aggregometer (PACKS 4, Helena Biosciences, Sunderland, UK). A control sample was run with each sample set. From the aggregation curves generated, the area under the curve was calculated for each PRP sample, and the inhibition of aggregation achieved at each inhibitor concentration was calculated by comparing the area under the curve for these PRP samples with that of the control sample. The inhibition of aggregation was expressed as % inhibition, compared to control, and from the 6 data points obtained per inhibitor compound, a dose-response curve was constructed. This curve was then used to predict the IC50 value for that inhibitor compound, as shown in 1.2, Results, and FIG. 1.

For each blood sample obtained, 6-point dose-response curves for 2 different inhibitory compounds could be generated. These experiments were repeated such that for each inhibitory compound, at least 3 (most often 7-10) different IC50 values were obtained on different days, using blood from different subjects (this applies to each agonist of interest). An average of the different IC50s was then taken and these values are quoted in 1.2, Results, Table 4.

1.2 Results

The physiochemical properties of the 32 compounds found to have most antiplatelet activity (see below) are summarised in Table 3.

TABLE 3

Physiochemical Properties of Bioactive Compounds identified in Fruit Extracts

| Group | Compound ID | Bioactive Compound | RT (s) | λ max | Mass/characteristic ions (POS mode) |
|---|---|---|---|---|---|
| Nucleosides | 1 | Cytidine | 1.24 | 275 | 487, 244 |
|  | 2 | Adenosine | 3.17 | 260 | 268, 136 |
|  | 3 | Uridine | 2.59 | 270 | 267, 113 |
|  | 4 | Guanosine | 3.9 | 260 (278 sh) | 284, 152 |
| Nucleotides | 5 | Adenosine 3'-monophospate | 1.6 | 260 | 348, 136 |
|  | 6 | Adenosine 5'-monophospate | 1.78 | 260 | 348, 136 |
| Phenolic acid glycosides | 7 | Mixed phenolic acid glycosides | 8.0-9.0 |  | Mixture |
|  | 8 | p-Coumaric acid hexose/quinic acid derivative | 9.02 | 300 | 469, 147, 119 |
|  | 9 | Caffeic acid glucoside | 9.39 | 290 | 319, 163 |
|  | 10 | Ferulic acid hexose | 9.67 | 295, 315 | 265, 177 |
|  | 11 | p-Coumaric acid hexose/dihydrokaempferol hexose mixture | 10.62 | 265 | 467, 449, 287; 450, 163 |
|  | 12 | p-Coumaric acid/caffeic acid conjugate, glycosylated | 11 | 285 | 367, 344, 163, 147 |
|  | 13 | Ferulic acid glycoside | 11 | 285, 315 sh | 379, 196, 177 |
|  | 14 | Chlorogenic acid | 12.77 | 325, 300 sh | 163, 377 |
| Phenolic ester derivatives | 15 | p-Coumaric acid derivative | 11.55 | 275 | 396, 196, 163 |
|  | 16 | Caffeoyl-quinic acid dimer #1 | 14.96 | 310 |  |
|  | 17 | Caffeoyl-quinic acid dimer #2 | 26.63 |  | 573, 814, 163 |
| Phenolic acids | 18 | Caffeic acid | 13.39 | 325, 295 sh | 163 |
|  | 19 | p-coumaric acid | 18.19 | 235, 310 | 165, 147, 119 |
|  | 20 | Benzoic acid | 22.36 |  |  |
|  | 21 | Ferulic acid | 22.61 |  | 177 |
|  | 22 | Cinnamic acid | 30.27 | 273 | 621, 599.5, 131.1 |
| Flavonoid glycosides | 23 | Quercetin-3-O-glycoside | 23.57 | 275 | 400, 303 |
|  | 24 | Kaempferol glycoside | 24.7 |  | 592, 535 |
|  | 25 | Quercetin-3-O-trisaccharides | 25.44 |  | 765, 453, 303 |
|  | 26 | Naringin | 25.88 | 285, 330 | 621, 563 |
|  | 27 | Rutin | 27.2 | 260, 350 | 633, 303 |
| Flavonoid ester derivatives | 28 | Flavonoid conjugate | 24.33 |  | 258 |
|  | 29 | Trace flavonoids + glycosides | 27.5-30.0 |  | Mixture |
| Flavonoids | 30 | Quercetin | 36.5 | 255, 370 | 629, 303, 273 |
|  | 31 | Kaempferol | 44.58 | 260, 370 | 287 |
|  | 32 | Naringenin | 35.1 |  |  |

Table 4 provides IC50 data (for inhibiting platelet aggregation) for the 32 compounds identified in the tomato extract. Activity was assayed as described in Method 1.1.4. FIG. 1 provides examples of dose-response curves of % inhibition of ADP-mediated aggregation versus inhibitor solution concentration generated for (a) a nucleoside (cytidine); (b) a nucleotide (adenosine 3' monophosphate; (c) a phenolic acid glycoside (Caffeic acid glucoside); (d) a phenolic acid (Caffeic acid); (e) a flavonoid glycoside (Quercetin-3-O-glycoside); and (f) a flavonoid (Quercetin).

TABLE 4

Antiplatelet Activity of Compounds identified in Fruit Extracts

| Group | Compound ID | Bioactive Compound | IC50 ADP | IC50 Collagen | IC50 TRAP | IC50 AA |
|---|---|---|---|---|---|---|
| Nucleosides | 1 | Cytidine | 2.42 | 10.66 | 39.03 | 39.03 |
|  | 2 | Adenosine | 0.4 | 0.82 | >50 | — |
|  | 3 | Uridine | 6.51 | 15.99 | >50 | — |
|  | 4 | Guanosine | 0.25 | 0.53 | 26.07 | 0.91 |
| Nucleotides | 5 | Adenosine 3'-monophospate | 0.12 | 0.28 | 24.51 | 2.41 |
|  | 6 | Adenosine 5'-monophospate | 0.12 | 0.28 | 24.51 | 2.41 |
| Phenolic acid glycosides | 7 | Mixed phenolic acid glycosides | N/A | N/A | N/A | N/A |
|  | 8 | p-Coumaric acid hexose/quinic acid derivative | 10.25 | 9.88 | 1.61 | 0.19 |

TABLE 4-continued

Antiplatelet Activity of Compounds identified in Fruit Extracts

| Group | Compound ID | Bioactive Compound | IC50 ADP | IC50 Collagen | IC50 TRAP | IC50 AA |
|---|---|---|---|---|---|---|
| | 9 | Caffeic acid glucoside | 10.16 | 8.22 | 0.8 | 0.23 |
| | 10 | Ferulic acid hexose | 12.61 | 14.16 | 0.52 | 0.46 |
| | 11 | p-Coumaric acid hexose/ dihydrokaempferol hexose mixture | 11.1 | 14 | 0.56 | 0.31 |
| | 12 | p-Coumaric acid/ caffeic acid conjugate, glycosylated | 12.61 | 13.18 | 0.25 | 0.2 |
| | 13 | Ferulic acid glycoside | 13.11 | 14.56 | 0.37 | 0.41 |
| | 14 | Chlorogenic acid | 10.08 | 10.11 | 1.1 | 0.77 |
| Phenolic ester derivatives | 15 | p-Coumaric acid derivative | 14.65 | 15.18 | 0.35 | 0.26 |
| | 16 | Caffeoyl-quinic acid dimer #1 | 31.55 | 35 | 11.12 | 0.3 |
| | 17 | Caffeoyl-quinic acid dimer #2 | 32.96 | 33.07 | 12.16 | 0.2 |
| Phenolic acids | 18 | Caffeic acid | 18.98 | 11.37 | 8.03 | 7.33 |
| | 19 | p-coumaric acid | 13.22 | 14.62 | 12.82 | 10.18 |
| | 20 | Benzoic acid | 25.11 | 17.74 | 18.19 | 15.45 |
| | 21 | Ferulic acid | 18.67 | 13.9 | 14.65 | 9.94 |
| | 22 | Cinnamic acid | 22.14 | 24.6 | 12.92 | 0.22 |
| Flavonoid glycosides | 23 | Quercetin-3-O-glycoside | 25.18 | 28.43 | 12.06 | 0.19 |
| | 24 | Kaempferol glycoside | >50 | >50 | N/A | N/A |
| | 25 | Quercetin-3-O-trisaccharides | >50 | >50 | 18.61 | 0.46 |
| | 26 | Naringin | 28.1 | 29.55 | 9.13 | 0.31 |
| | 27 | Rutin | 35.21 | 32.18 | 8.96 | 0.41 |
| Flavonoid ester derivatives | 28 | Flavonoid conjugate | 27.68 | 27.22 | 13.67 | 0.23 |
| | 29 | Trace flavonoids + glycosides | N/A | N/A | N/A | N/A |
| Flavonoids | 30 | Quercetin | >50 | >50 | 19.66 | 3.66 |
| | 31 | Kaempferol | >50 | >50 | 26.18 | 5.18 |
| | 32 | Naringenin | >50 | >50 | 33.21 | 10.41 |

1.3 Conclusions

The inventors tested a number of compound found within tomato extracts and established that the 32 compounds identified in tables 2 and 3 had efficacy for preventing platelet aggregation. Furthermore they concluded that, of the 32 compounds isolated and shown to have anti-aggregatory capacity, 16 of these compounds were most important for overall bioactivity. These 16 compounds are shown in Table 1.

In particular they were surprised to find that the bioactive compounds could be grouped into (a) phenolic compounds (and ester and glycoside derivatives thereof); (b) flavonoids (and ester and glycoside derivatives thereof) and (c) nucleotides/nucleosides. This lead them to realise that two new classes of compounds (the phenolics and flavonoids) exist which have an inhibitory effect on platelet aggregation.

Of these compounds, the most anti-aggregatory of the non-phenolic compounds was AMP. Modification of the nucleoside by sugar and phosphate residues had the effect of substantially increasing the anti-aggregatory behaviour. This was surprising as earlier work had identified cytidine and adenosine as antiplatelet constituents, but no nucleotides.

Of the phenolic acid-derived compounds identified, the most anti-aggregatory overall were the glycosylated forms of p-coumaric and caffeic acids. These glycosylated compounds showed markedly higher anti-aggregatory potential in response to all agonists tested, compared to the non-glycosylated free acids. This is the first time such a structure-function relationship has been reported. Accordingly glycosylated phenolic compounds represent most preferred bioactive molecules that may be contained with the extracts according to the invention and which should be maintained/enriched in extracts prepared according to the method of first aspect of the invention.

A similar finding was made with regard to the flavonoid derivatives. The glycosides or other conjugated derivatives of quercetin and naringenin were markedly more anti-aggregatory than the flavonoid aglycones. This was particularly noticeable in response to TRAP and arachidonic acid agonists, but also applied to ADP and collagen agonists. While a (very limited) amount of structure-function studies have been reported in the literature for the free flavonoid aglycones, the authors are unaware of any studies comparing aglycones and conjugated molecules. Accordingly glycosylated flavonoid compounds also represent most preferred bioactive molecules that may be contained with the extracts according to the invention and which should be maintained/enriched in extracts prepared according to the method of the first aspect of the invention.

It was interesting to note that when the ratio of AMP to adenosine decreased, the overall bioactivity of the extract decreased. The same was found to happen when the ratio of phenolic acid glycosides/esters to free phenolic acids decreased, and when the ratio of flavonoid glycosides to free flavonoids decreased.

It is worth noting that a simple way of producing a fruit extract according to the third aspect of the invention is disclosed in 1.1.3. An extract prepared according to the methods disclosed in WO 99/55350 may be fractionated to isolate three fractions which were identified as having anti-platelet activity. Fraction 1 contained largely nucleosides and nucleotides. Fraction 2 contained largely phenolic acid glycosides/esters, and phenolic acids. Fraction 3 contained largely flavonoid glycosides and flavonoids. These three fractions can then be recombined (fraction 1+2+3) to provide an extract according to the third aspect of the invention which has surprising efficacy.

EXAMPLE 2

In view of the knowledge gained with regards active compounds within tomato extracts. The inventors proceeded to develop methods of processing fruits to produce extracts in which the activity of the compounds was maintained and/or in which the concentration of such active compounds was enriched.

After much experimentation the inventors established that the methodology according to the first aspect of the invention was optimal for producing extracts enriched in a significant number of the active compounds identified in Example 1.

Having established this methodology the inventors went on to develop a process that could be used in the industrial scale-up of the methods of the invention to produce a syrup that may be used in the manufacture of pharmaceutical or food products (drinks or food stuffs).

Figure 2:
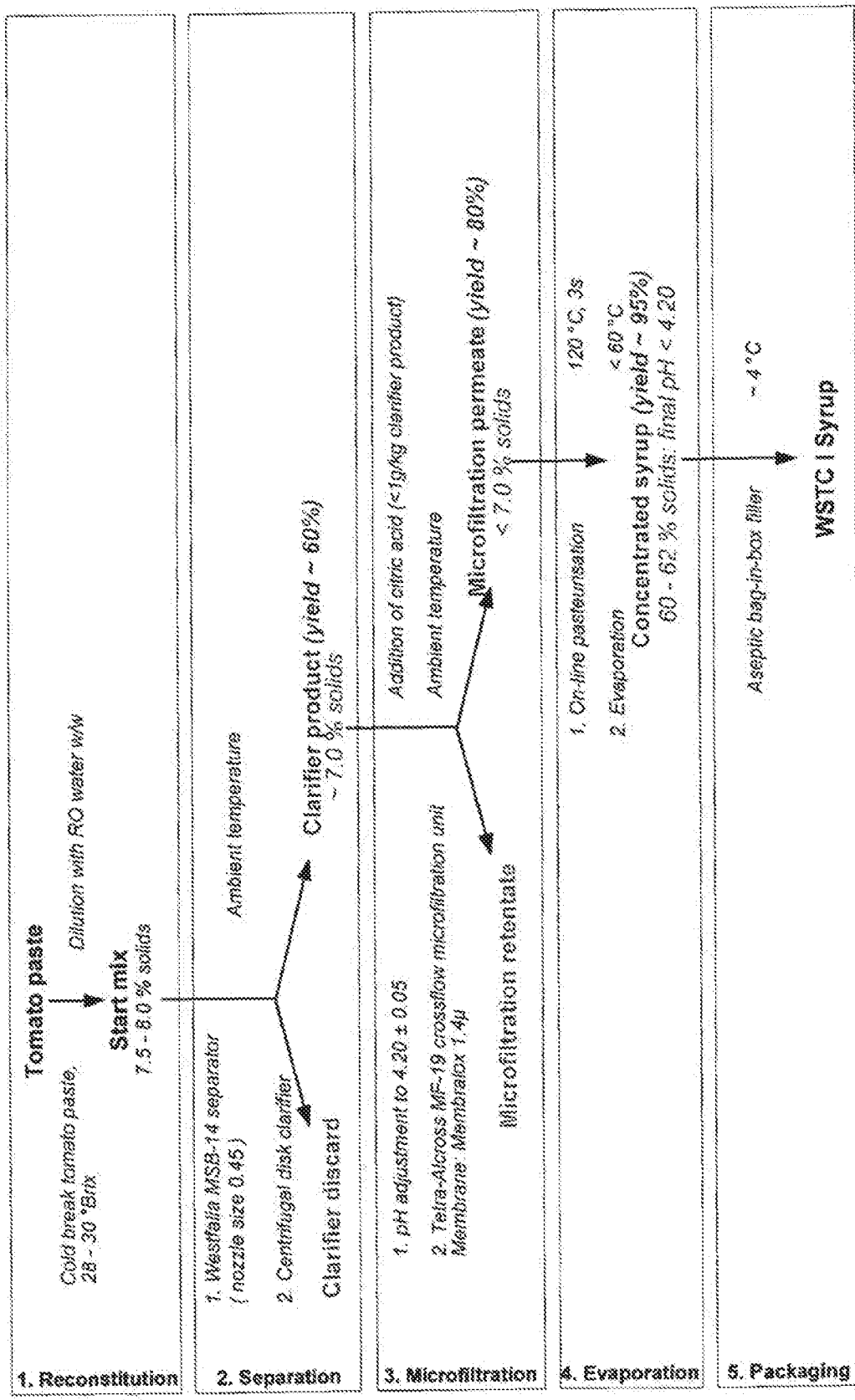
FIG. 2: defines a preferred method according to the first aspect of the invention for making fruit extracts as discussed in Example 2.

The process for making such a syrup is illustrated in FIG. 2 and represents a preferred embodiment of the first aspect of the invention.

Syrups prepared according to the process of FIG. 2 represent a most preferred extract according to the second or third aspect of the invention and have the properties defined in Table 2 (see above) and also Table 5.

TABLE 5

Composition of a most preferred Tomato Extract according to the second or third aspects of the invention.

| Specification Parameter | Specification |
|---|---|
| Dry Matter (° Brix) | 60 to 63 |
| Density (g/cm$^3$) | 1.15 to 1.22 |
| pH (at 4° Brix) | 3.90 to 4.15 |
| Browning index (at 4° Brix) | <0.70 |
| Total Carbohydrates (g/100 g) | 58 to 70 |
| Pectin (g/100 g) | 33 to 40 |
| Reducing Sugars (g/100 g) | 22 to 30 |
| Protein (g/100 g) | 4 to 6 |
| Free Amino Acids (g/100 g) | 2 to 3.5 |
| Bioactive compounds (g/100 g) | 3.0 to 4.0 |
| Total viable count (CFU/mL) | <1,000 |
| *Salmonella* (CFU/25 mL) | Absent |
| *Listeria monocytogoenes* (CFU/25 mL) | Absent |
| *Staphylococcus aureus* (CFU/mL) | Absent |
| *Enterobacteria* (CFU/mL) | <10 |
| Yeasts and molds (CFU/mL) | <1,000 |

The syrup may contain up to 70% dry matter simple sugars (glucose, fructose and sucrose) and may contain up to 50% water.

Figure 3:
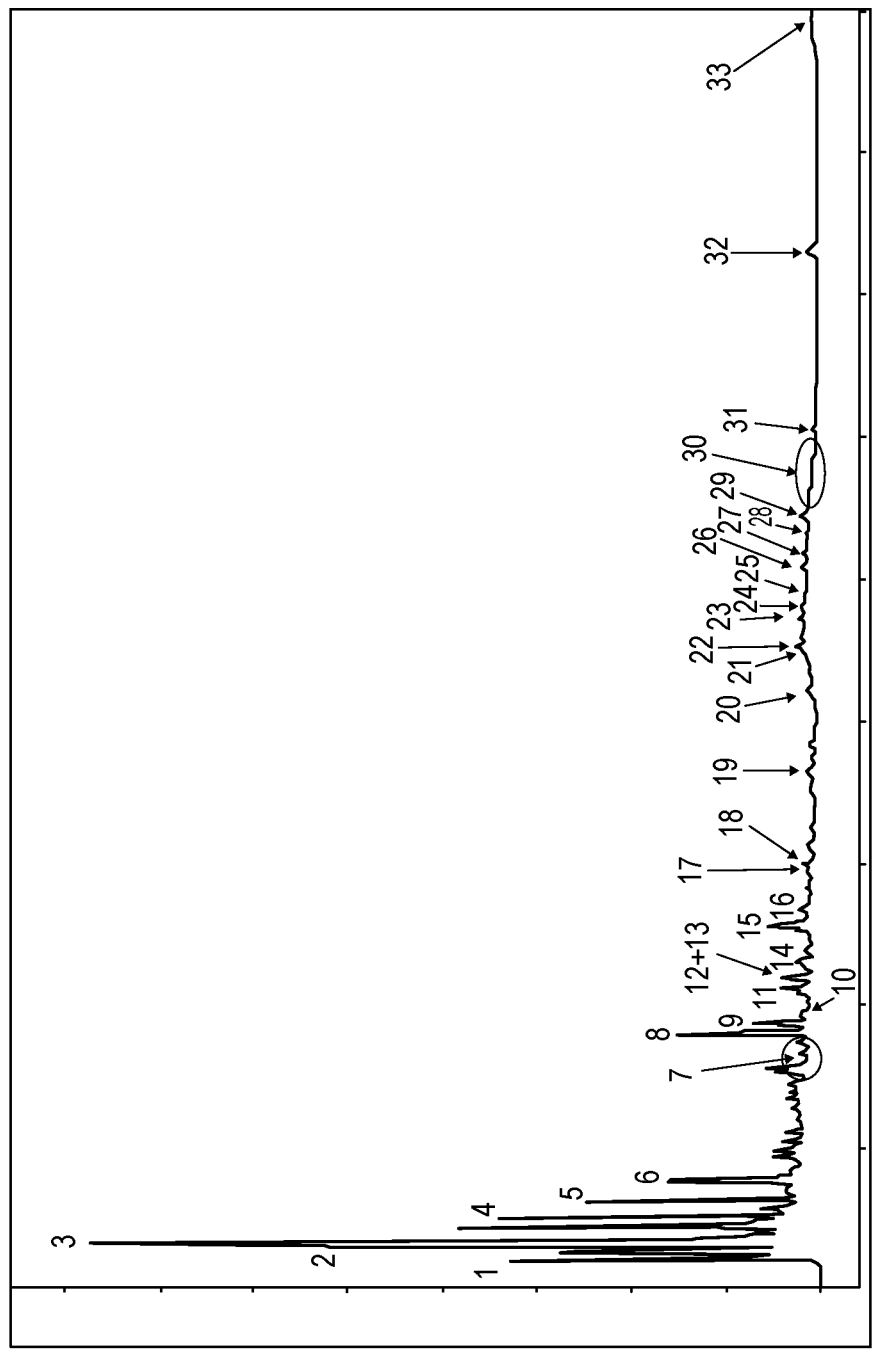
FIG. 3: is an HPLC chromatogram of syrup produced using the method detailed in Example 2. Bioactive compounds are numbered on the chromatogram.

Most preferred Syrups produced using this method contain up to 32 bioactive components, which are numbered in the HPLC chromatogram shown in FIG. 3 and correspond to the numbered compounds identified in Table 1-4 and discussed in Example 1.

Some additional characteristics of the syrups, which are important in optimising their bioactivity profile, are provided in table 6 (below). Compound numbers refer to the chromatogram shown in FIG. 3 and the compounds identified in Table 1-4.

TABLE 6

| Compound ID | Specification |
|---|---|
| Compounds 2-6 | >2.00 mg/g |
| Compound 8 | >0.05 mg/g |
| Compound 9 | >0.07 mg/g |
| Compound 10 | >0.03 mg/g |
| Compound 11 | >0.30 mg/g |
| Compound 12 | >0.20 mg/g |
| Compound 13 | >0.16 mg/g |
| Compound 14 | >0.13 mg/g |
| Compound 15 | >0.10 mg/g |
| Compound 23 | >0.05 mg/g |
| Compound 25 | >0.16 mg/g |
| Compound 26 | >0.74 mg/g |
| Compound 27 | >0.60 mg/g |
| Compounds 18, 19 & 21 | <1.50 mg/g |
| Compound 5: Compound 2 ratio | >3.0 |
| Glutamine | >8.00 mg/g |
| Furfural derivatives | <0.15 mg/g |

The inventors recognised that the characteristics outlined in Table 6 were important when optimising anti-platelet activity of extracts according to the invention. Most preferred extracts according to the second or third aspects of the invention have these properties. Furthermore these characteristics can be used as Quality control measures in most preferred embodiments of the methods of the first aspect of the invention. Therefore these characteristics are particularly useful control point when extracts are produced on an industrial scale.

EXAMPLE 3

The inventors also developed a process that could be used in the industrial scale-up of the methods of the invention for the production of a low-sugar fruit extract in the form of a powder. The powder may also be used in the manufacture of pharmaceutical or food products (drinks or food stuffs).

Figure 4A:
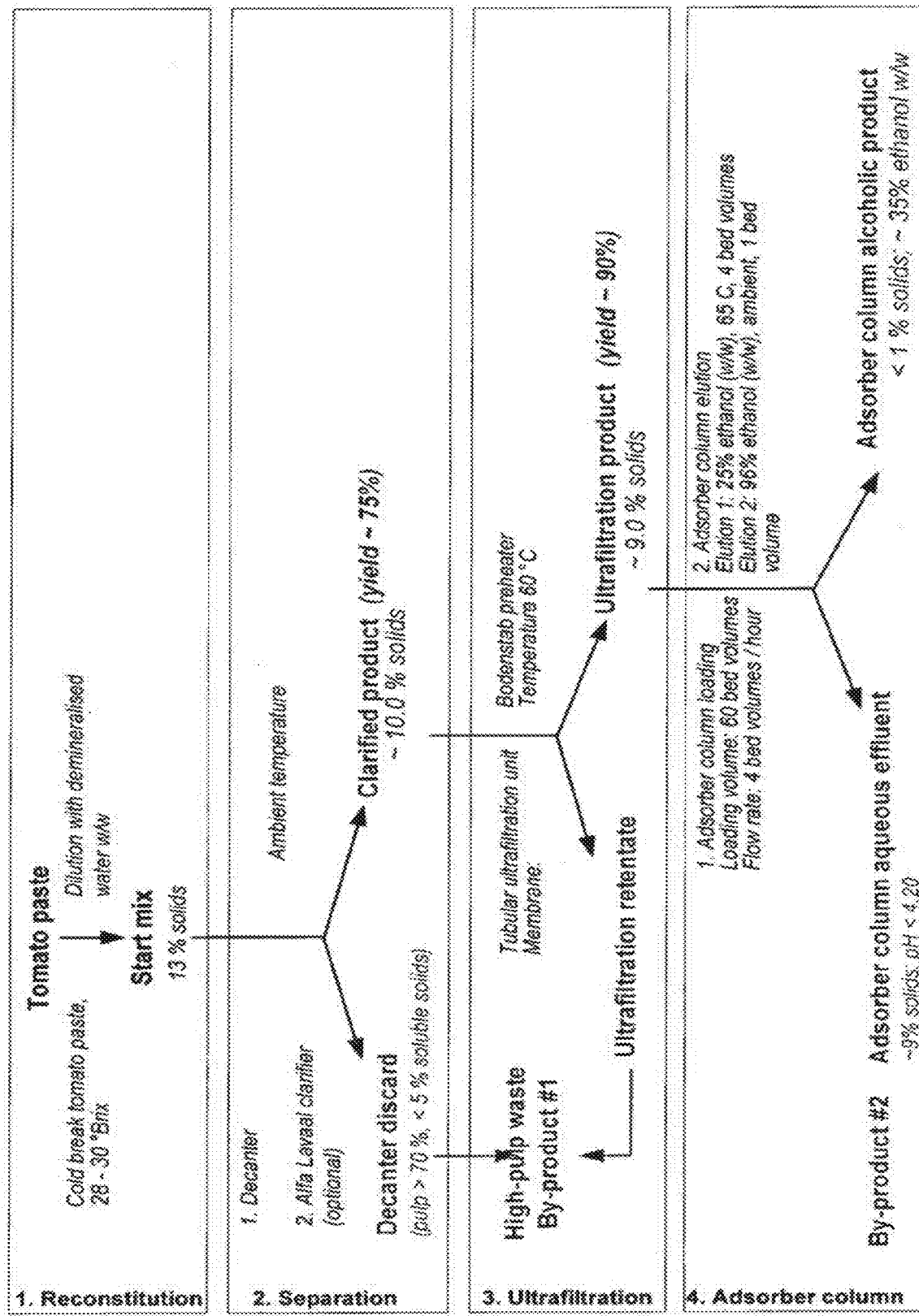
FIG. 4A-4B: defines a preferred method according to the first aspect of the invention for making low sugar fruit extracts as discussed in Example 3. 4A shows steps 1-4; 4B shows steps 5-7.
Figure 4B:
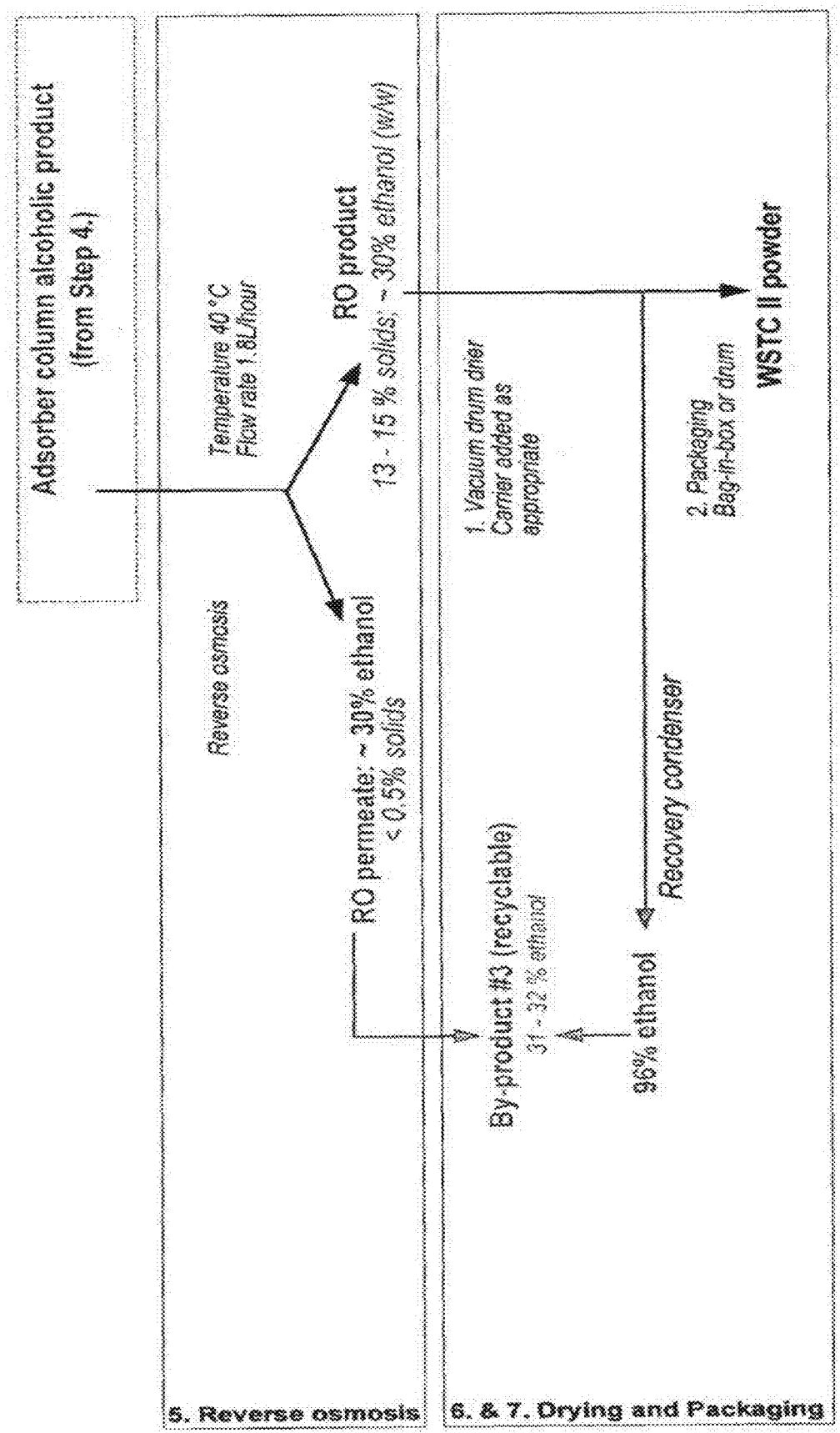

A process for producing such a powder is illustrated in FIG. 4 and represents a preferred embodiment of the first aspect of the invention.

Extracts prepared according to the process of FIG. 4 also represent preferred extracts according to the second or third aspect.

Extracts prepared according to the process of FIG. 4 represent a preferred extract according to the second or third aspect of the invention and have the properties defined in Table 2 (see above) and also Table 7.

TABLE 7

Composition of a most preferred low sugar Tomato Extract according to the second or third aspects of the invention

| Specification Parameter | Specification |
|---|---|
| Dry Matter (% w/w) | 94 to 96 |
| Bulk density (g/cm$^3$) | 0.25 to 0.30 |
| PH (in water at 4° Brix) | 3.5 to 3.8 |
| Browning index (in water at 4° Brix) | <3.00 |
| Total Carbohydrates (g/100 g) | <0.1 |
| Pectin (g/100 g) | — |
| Reducing Sugars (g/100 g) | <0.1 |
| Protein (g/100 g) | <0.01 |
| Free Amino Acids (g/100 g) | 30 to 37 |
| Bioactive compounds (g/100 g) | 50 to 60 |
| Total viable count (CFU/mL) | <1,000 |
| *Salmonella* (CFU/25 mL) | Absent |
| *Listeria monocytogoenes* (CFU/25 mL) | Absent |
| *Staphylococcus aureus* (CFU/mL) | Absent |
| *Enterobacteria* (CFU/mL) | <10 |
| Yeasts and molds (CFU/mL) | <1,000 |

The powder may contain less than 1% dry matter simple sugars (glucose, fructose and sucrose) and may contain <6% water. The enriched powder extract typically contains up to 60% bioactive compounds.

Figure 5:
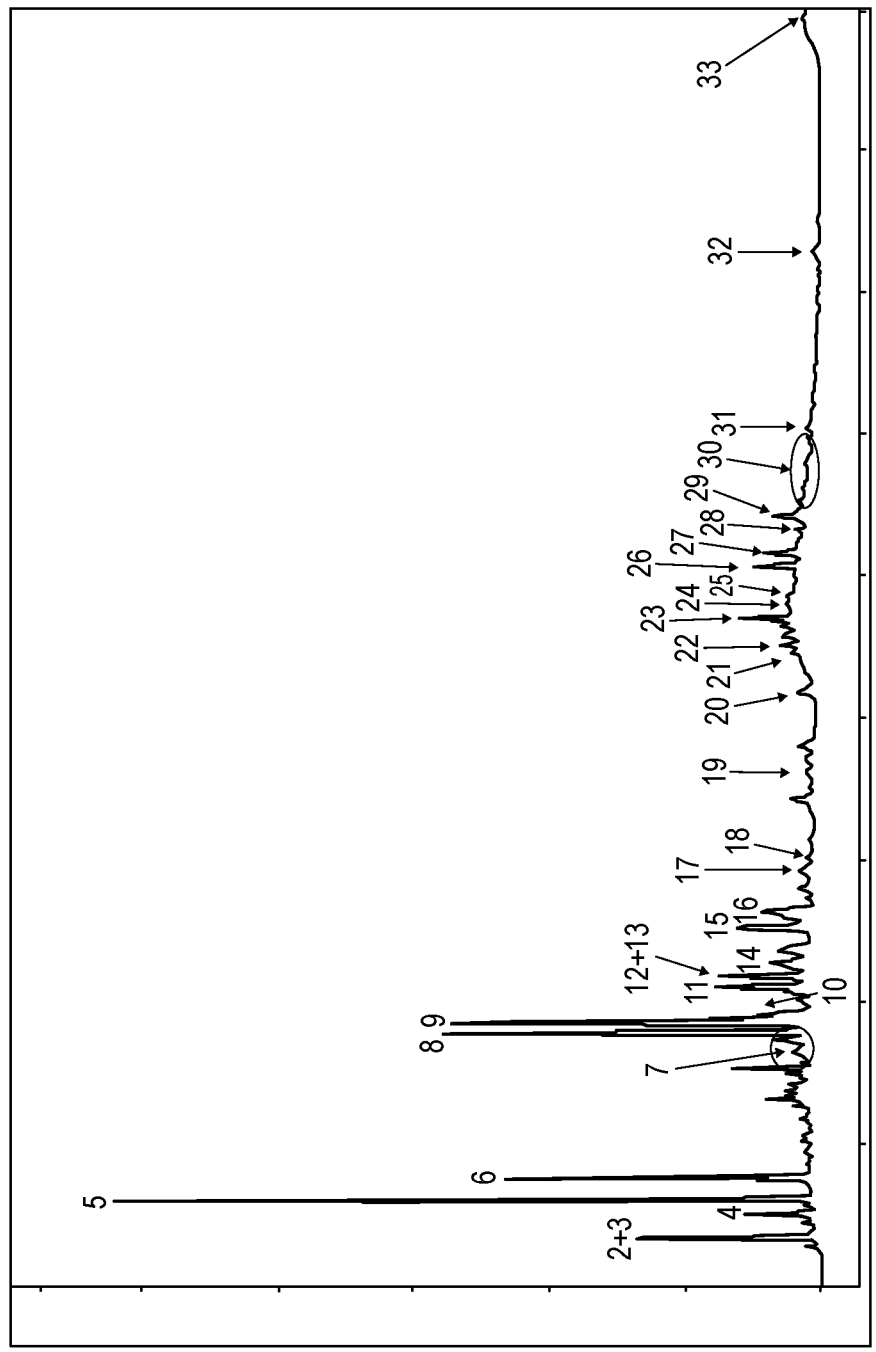
FIG. 5: is an HPLC chromatogram of syrup produced using the method detailed in Example 3. Bioactive compounds are numbered on the chromatogram.

Extracts produced using this method also contain up to 33 different bioactive components, which are numbered in the HPLC chromatogram shown in FIG. 5 and correspond to the numbered compounds identified in Tables 1-4 and as discussed in Example 1.

Some additional characteristics of these powders, which are important in optimising their bioactivity profile, are given in Table 8. Compound numbers refer to the chromatogram shown in FIG. 5 and tables 1-4.

TABLE 8

| Compound ID | Specification |
| --- | --- |
| Compounds 2-6 | >15.20 mg/g |
| Compound 8 | >9.40 mg/g |
| Compound 9 | >3.70 mg/g |
| Compound 10 | >0.70 mg/g |
| Compound 11 | >26.10 mg/g |
| Compound 12 | >90.80 mg/g |
| Compound 13 | >85.30 mg/g |
| Compound 14 | >18.30 mg/g |
| Compound 15 | >8.60 mg/g |
| Compound 23 | >8.50 mg/g |
| Compound 25 | >14.70 mg/g |
| Compound 26 | >38.00 mg/g |
| Compound 27 | >50.70 mg/g |
| Compounds 18, 19 & 21 | <38.00 mg/g |
| Compound 1: Compound 3 ratio | >3.0 |
| Glutamine | >52.00 mg/g |
| Furfural derivatives | <0.50 mg/g |

The inventors recognised that the characteristics outlined in Table 8 were important when optimising anti-platelet activity of extracts according to the invention. Most preferred extracts according to the second or third aspects of the invention have these properties. Furthermore these characteristics can be used as Quality control measures in most preferred embodiments of the methods of the first aspect of the invention. Therefore these characteristics are particularly useful control point when extracts are produced on an industrial scale.

EXAMPLE 4

In the following Example, an experiment is described in which the anti-platelet efficacy of a composition prepared according to the methods described in Example 2 was tested. It will be appreciated that compositions prepared according the methods described in Example 3 could be tested following the same protocol.

4.1 Study Protocol 4.1.1 Study Objectives and Short Outline

This study Quantified the ex vivo antiplatelet effect of consuming a treatment drink containing 3 g of tomato extract syrup (prepared according to the methods described in Example 2), compared to a control supplement, in healthy subjects.

4.1.2 Study Design

A single-blinded study design was followed. Fasted subjects were cannulated and a baseline sample was taken between 07:00 and 08:00. Directly after collection of the baseline sample, subjects consumed either a treatment (TE) or a control supplement. Further blood samples were then withdrawn from the cannula at time t=3 hours. Subjects were offered small volumes (25 mL) of water between sampling time points to avoid dehydration.

4.1.3 Subjects 9 healthy adults of both sexes were recruited into the study. Subjects were aged 40-65 years, with no medical history of serious disease or hemostatic disorders. Suitability for inclusion onto the study was assessed by diet and lifestyle questionnaires and medical screening, during which a full blood count was obtained. Individuals with low hematology counts were not included in the study. Any subjects habitually consuming dietary supplements (e.g. fish oils, evening primrose oil) suspended these supplements for a minimum period of one month before participating in the study. Subjects were instructed to abstain from consuming drugs known to affect platelet function for a 10-day period prior to participation. Written informed consent was obtained from all subjects, and the study was approved by Grampian Research Ethics Committee.

4.1.4 Phlebotomy

Subjects recruited into the study were cannulated using a siliconized 21-gauge butterfly needle, to cause minimum disruption to the vein while taking multiple blood samples. To minimize activation of the hemostatic system, a maximum of three venepunctures was specified. The cannula remained in place over the entire study time period, and venous blood samples of ~30 mL were withdrawn at each sampling timepoint, discarding the first 2 mL on each occasion. After blood sample collection, the cannula was flushed with saline to prevent blockage. For measurements of platelet function and clotting time, blood was collected into plastic syringes and transferred into citrated blood collection tubes (final concentration sodium citrate, 13 mmol/L). For measurement of C-reactive protein (CRP), a single baseline blood sample (5 mL) was taken into EDTA anticoagulant (final concentration, 1.6 g/L). For measurement of fibrinopeptide A at each timepoint, 4.5 mL blood was collected into 0.5 mL of a mixed anticoagulant containing EDTA, trasylol and chloromethylketone. Blood samples were incubated at 37° C. in a portable incubator for transfer to the laboratory. Any blood samples showing evidence of activation, defined as a fibrinopeptide A concentration higher than 6 µg/L, were discarded. Any volunteers showing evidence of an elevated inflammatory response, as evidenced by a baseline C-reactive protein concentration higher than 6 mg/L, were withdrawn from the study for the period affected, and the scheduled intervention was undertaken at a later date.

4.1.5 Ex Vivo Platelet Aggregation Studies

Measurement of the extent of ADP and collagen-induced platelet aggregation in platelet-rich plasma was carried out at each timepoint. Different agonist concentrations may be used to approximate different physiological conditions. In order to collect data under conditions of suboptimal platelet stimulation, a standardized lower concentration (3 µmol/L for ADP, 3 mg/L for collagen) was defined as suboptimal, while a standardised upper concentration (7.5 µmol/L for ADP, 5 mg/L for collagen) was defined as optimal. These agonist concentrations were used for all measurements. Effects on platelet aggregation observed after treatment or control interventions are expressed as the percentage change in area under the aggregation curve after consumption of extract/placebo, compared to baseline values.

4.1.6 Supplementary Measurements

Detection of high plasma CRP was carried out using a semi-quantitative latex agglutination assay (Dade Behring, UK), which detected levels in plasma >6 mg/L. This threshold is taken as an indication of acute inflammatory system activation, such as may be associated with infection (e.g. onset of a viral infection or a cold) or injury (e.g. tendonitis). Samples displaying signs of such acute activation should not be used for platelet function studies.

Measurement of FPA was carried out by ELISA (Zymutest FPA assay, HyphenBioMed, France), on plasma from which fibrinogen had been removed by bentonite adsorption treatments. Presence of FPA in plasma at levels greater than 6 µg/L was taken as an indication of haemostatic system activation during blood sampling. Such samples should not be used for platelet function measurement as results obtained will not be reliable. Thus circulating CRP levels and blood sample FPA levels were used to indicate suitability of samples for platelet measurements.

4.2 Results

No blood samples drawn during this study displayed levels of circulating CRP higher than the threshold 6 mg/L, indicating that acute phase activation was not present in any subject during the study sampling days. Similarly, in blood samples drawn for this study, no samples showed FPA levels higher than the threshold 6 µg/L. Thus all blood samples received were judged suitable for platelet function studies. This screening data is not included.

Figure 6:
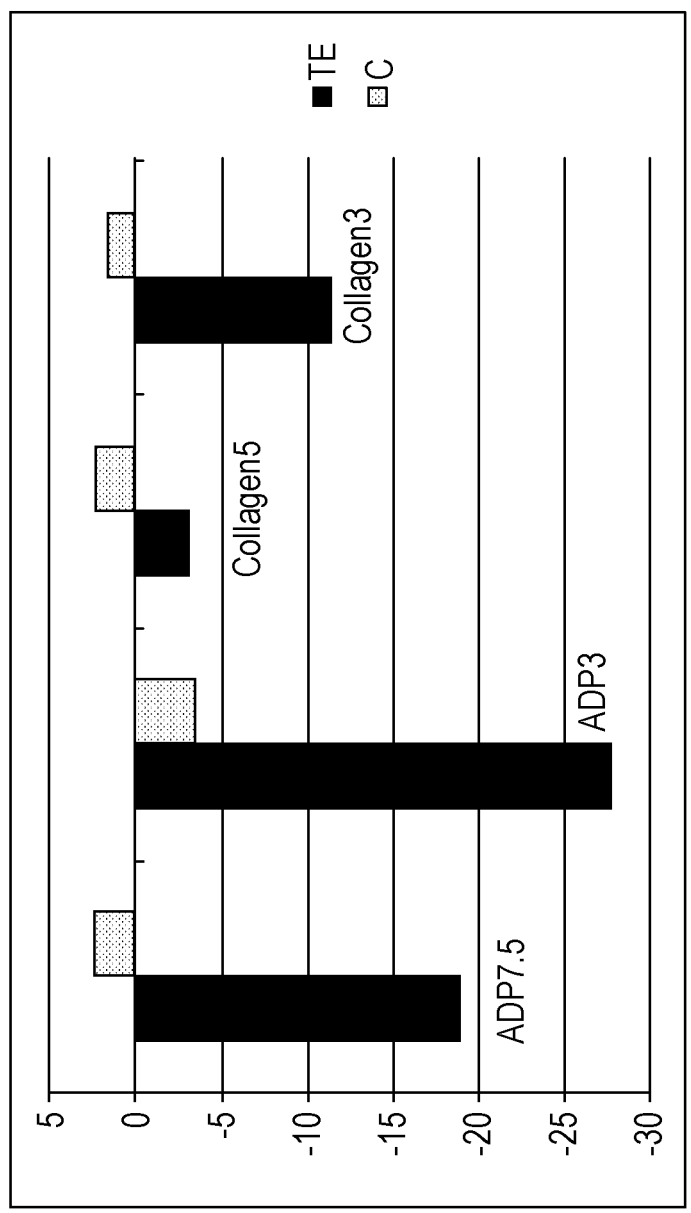
FIG. 6: % Change from baseline aggregation in response to different platelet agonists, 3 hours after consumption of tomato extract (TE) or control (C) supplements, as described in Example 4. The platelet agonists used were adenosine diphosphate (ADP) 7.5 µmol/L and 3 µmol/L, and collagen 5 mg/L and 3 mg/L. Significant differences between TE and C supplements are indicated on the graph (P<0.001). N=9 for all measurements.

The data presented in FIG. 6 illustrate platelet aggregation measurements carried out at baseline (t=0) and at 3 hours post-consumption of treatment supplements (t=3). Results are expressed as % inhibition of platelet aggregability, compared to baseline values.

4.3 Conclusions

FIG. 6 demonstrates that tomato extracts according to the invention result in a reduction from baseline platelet aggregation of between 18% and 28% for ADP mediated aggregation, and between 3% and 12% for collagen mediated aggregation, 3 hours after consumption. Consumption of the control supplement resulted in a change from baseline aggregation of between 2% and 4% for ADP-mediated aggregation, and approximately 2% for collagen-mediated aggregation, after 3 hours. The differences between baseline and 3-hour time points were not significant for the control supplement, but were significant at $P<0.001$ for the tomato extract supplement. Differences between the control and tomato extract supplements were also significant at the $P<0.001$ level.

These results clearly demonstrate that tomato extracts according to the invention are useful for treating conditions characterised by inappropriate platelet aggregation.

Furthermore the inventors have established that the methods according to the invention result in the production new tomato extracts with improved properties when compared to known tomato extracts (e.g. those disclosed in WO 99/55350). The inventors compared ex vivo antiplatelet activity measured after eating tomato extract produced by known processing method, and tomato extract produced using the methods according to the present invention which target maintenance of glycosides and esters. They found that a single dose of 3 g of tomato extract according to the present invention resulted in an inhibition of 3 µmol/L ADP-induced platelet aggregation of 28% compared to baseline whereas, known extracts result in an inhibition of ADP-induced platelet aggregation of ~25% although this is only achieved by consuming 9 g of extract. Thus the methods of the present invention appear to enrich bioactives in the extract by approximately 3 times. According employment of the methods of the first aspect of the invention result in a more potent extract and, advantageously, the necessary daily dose may be reduced.

EXAMPLE 5

The inventors prepared a number of products that represent preferred formulations comprising extracts according to the invention.

Yoghurt Drinks Containing Tomato Extracts

The tomato extracts prepared as described in Examples 2 and 3 are both suitable for incorporation into a yoghurt drink. An example of such a drink may be prepared as follows.

Drinking yoghurt, formulated without live probiotic cultures, should be pre-pasteurised and cooled to 4-8° C. The cooled yoghurt should be mixed with tomato extract as prepared in Example 2 in the ratio 50:1, or with tomato extract as prepared in Example 3 in the ratio 1000:1 (w/w). Acidity should be checked and regulated with citric acid, and flavouring should be adjusted. If a probiotic culture is required in the final product, this should be added after adjustment, and the final mixture should be packaged into single-serve 150 g bottles.

Each single-serve 150 g bottle should then contain either 3 g tomato extract prepared according to Example 2, or 150 mg tomato extract prepared according to Example 3. This represents a single daily dose. The final products should be stored at 4° C. for their recommended shelf life (typically between 14 and 21 days).

Fat Spreads Containing Tomato Extract

Tomato extract prepared as described in Example 3, or further processed to give an encapsulate, is suitable for incorporation into fat spreads. An example of such a formulation may be produced by post-pasteurisation dosing the powdered, low-sugar tomato extract into pre-formulated, pasteurised and cooled fat spread in the ratio 200:1 (w/w). The mixture should be homogenised at high shear to ensure homogenous distribution, and packaged into multi-serve containers.

Label text should include the information that the normal daily intake of fat spread should be approximately 30 g. Consumption of 30 g fat spread per day will result in a daily intake of approximately 150 mg tomato extract, which constitutes a single daily dose. The spread should be stored at 4° C. for the duration of its shelf life (typically 90 days).

Fruit Juice-Based Drinks Containing Tomato Extracts

The tomato extracts prepared as described in Examples 2 and 3 are both suitable for incorporation into a fruit-juice based drinks. An example of such a drink may be prepared as follows.

Dilute orange juice concentrate with water in the ratio 1:5.4. To the reconstituted juice, add 0.1% grapefruit flavour, 0.05% pineapple flavour, and 1.2% tomato extract as produced in Example 2. Test acidity and sweetness, and add up to 5% citric acid (acidity regulator) and up to 2% sucralose, as required. Pasteurise for 90 seconds at 121° C.

Package the pasteurised mixture in 1 L cartons, or in single-serve cartons or bottles. 250 mL of the final drink as described should contain approximately 3 g tomato extract, equivalent to a single daily dose. Label details should contain this information and the advice to drink one 250 mL portion per day.

Other fruit juice concentrates are equally appropriate for use; alternatively fresh fruit juices, mixtures of fruit and vegetable juices, or mixtures containing variable amounts of pulp, may be prepared.

Encapsulates

Prepare a 50% w/w solution of powdered, low-sugar tomato extract which has been manufactured as described in Example 3. Raise the temperature to 60° C. Mix with an equal volume of either: a melted and emulsified mixture of high-melting fats, e.g. triglycerides; a solution of dispersed polysaccharides, e.g. pectins, agars; or other suitable polymers. Homogenise with care to ensure correct blending. Produce an encapsulate using a technique such as temperature-controlled spray-drying, controlling particle size so that final particle size is <200µ. Additives such as colours, preservatives or free-flow agents may be added to the dispersion prior to spray drying, as appropriate.

The resulting encapsulate should contain between 12% and 20% tomato extract on a w/w basis. The encapsulate should be stored at <4° C., in the dark, in sealed foil wrapping materials. Dosage of the encapsulate should be in the range 400 mg-700 mg per day, when incorporated into food products.

Sacheted Ready-to-Dissolve Formulations

The tomato extract as described in Example 3 is suitable for incorporation into pre-mixed, ready-to-dissolve single serving sachet formulations. An example of such a formulation may be prepared by mixing: 150 mg powdered, low-sugar tomato extract; 285 g maltodextrin; 6.5 g strawberry cream flavour; 0.8 g sucralose; 3.8 g citric acid; 2.5 g natural beet red colour; and 0.25 g caramel. The resulting ~300 g dry powder mix can be presented in a single-serve foil-backed sachet, suitable for dissolving in between 50 mL and 300 mL water, to taste. Each 300 g mixture contains a single daily dose of tomato extract.

The powdered, sacheted formulation should be stored at room temperature, and presented with instructions to consume one sachet per day in water.

Tablets

The tomato extract as described in Example 2 may used to prepare tablets for pharmaceutical or dietary supplement use, e.g. tabletting by direct compression, as follows.

The tomato extract as described in Example 2 should be milled/ground to a particle size range of 1-3µ prior to tabletting. The pre-ground powdered extract should be dry-blended with an excipient such as microcrystalline cellulose, or maltodextrin M700, to provide lubrication during the compression process. A ratio of 40% extract to 60% excipient is suitable, but ratios from 10:90 to 60:40 may also be used. Powdered colourants may also be added as required.

Using a conventional tabletting machine, set at a pressure of 1.5-2.0 tonnes/square inch, 212 g tablets of 5 kg hardness may be produced. Such tablets will contain 85 mg tomato extract per tablet. Storage in laminated aluminium foil blister packs is recommended. In such packaging, tablets will be stable to storage under temperatures up to 45 C. Two tablets should be taken together, once or twice per day, to achieve a recommended dosage level.

EXAMPLE 6

In Example 4 the direct antiplatelet effects of a composition prepared according to the methods described in Example 2 were described. To illustrate that these antiplatelet effects are of a magnitude to affect blood fluidity or blood flow, further work was undertaken in which the effects of this composition on overall primary haemostasis was measured. Haemostasis, that is, the halting of bleeding by the clotting process, occurs in two parts. Primary haemostasis refers to the ability of whole blood to form platelet micro- and macro-aggregates under flowing conditions, and form an initial platelet clot on a collagen-rich surface (normally a blood vessel wall). Secondary haemostasis refers to the formation of a fibrin network in this primary clot, induced by thrombin, which leads to a more permanent clot which takes significant time to dissolve via fibrinolysis. Measurement of primary haemostasis gives data that may be more physiologically relevant than aggregation data alone, when examining the efficacy of the tomato extract composition in affecting blood fluidity and thus blood flow.

In the following Example, an experiment is described in which the effect on overall primary haemostasis of a composition prepared according to the methods described in Example 2 was tested, using a Platelet Function Analyser, the PFA-100®. The platelet function analyzer device has become a useful tool for measurement of primary hemostasis in small samples of blood. This test system is a microprocessor controlled instrument which emulates in vitro the platelet dependent phase of primary hemostasis, while delimiting the role of the rheological factors. Basically, the system monitors platelet interaction on collagen-ADP (COL-ADP) or collagen-epinephrine (COL-EPI) coated membranes. Samples of citrated blood are aspirated under controlled flow conditions (shear rate: 4,000-5,000/s) through a 150-micrometer aperture cut into the membrane. During the process, the growing platelet plug progressively blocks the blood flow through the aperture cut. The platelet hemostatic capacity in the blood sample is indicated by the time required for the platelet plug to occlude the aperture (closure time), which is expressed in seconds.

6.1 Study Protocol 6.1.1 Study Objectives and Short Outline

This study examined the ex vivo effect of consuming 3 g of tomato extract syrup (prepared according to the methods described in Example 2), compared to a control supplement, on primary haemostasis in healthy subjects.

6.1.2 Study Design 6 healthy adults aged 45-75 years, with normal hemostatic parameters (blood counts), no medical history of serious disease or hemostatic disorders, and not consuming dietary supplements or drugs known to affect platelet function, were recruited. Written informed consent was obtained, and the study was approved by Grampian Research Ethics Committee. Baseline blood samples (anticoagulated with acid citrate dextrose buffer) were taken from fasted subjects between 07:00 and 08:30. Directly after collection of the baseline sample, subjects consumed either a treatment (TE) or a control supplement. Further blood samples were then taken at time t=3 hours, and t=5 hours after supplementation.

6.1.5 Ex Vivo Measurement of Primary Haemostasis

Measurement of PFA-1 00 closure time in whole blood samples was carried out at each timepoint. Measurements were carried out using collagen-epinephrine membranes. Briefly, cartridges containing the appropriate membranes were brought to room temperature, and 900 tJI of anticoagulated whole blood was inserted into the reservoir of each cartridge. The cartridges were then immediately inserted into the processing unit of the PFA-100. The blood was aspirated automatically from the reservoir through the cartridge membrane at high shear, until the membrane aperture was closed (closure time) or for a maximum of 300 s in the event that no clot was formed. Closure times were recorded and a printout produced. All measurements were carried out a minimum of 30 minutes after blood sampling.

6.2 Results

Average closure times for each treatment are presented graphically in FIG. 7. In this Figure recorded average closure times are shown for the baseline (time 0 relative to supplementation with treatment (TE) or control (C)), and at 3 hours and 5 hours after supplementation with TE or C. n=3 for each group, and data were analysed by ANOVA. Significant differences between C and TE are indicated on the graph by * (P=0.011).

6.3 Conclusions

Results demonstrate that tomato extracts representing compositions according to the invention result in an average increase in PFA-100 closure time of 24% from baseline values, 3 and 5 hours after consumption. Consumption of the control supplement resulted in an average decrease from baseline closure times of 16% after 3 hours, and 12% after 5 hours. The differences between baseline and 3 and 5-hour time points were not significant for the control supplement, but were significant at P=0.011 for the tomato extract supplement. Differences between the control and tomato extract supplements were significant (P=0.011).

The results show that the tomato extract supplement compositions in accordance with the invention increase the time taken for a platelet clot to form in each cartridge aperture, implying that the platelet hemostatic potential has decreased. The longer time required for a clot to form reflects a higher blood fluidity.

These results clearly demonstrate that compositions (such as tomato extracts) according to the invention are useful in reducing blood fluidity. This supports their use in normalising blood flow.

The invention claimed is:

1. A method of making an extract of fruit of the Solanaceae family, wherein the extract of Solanaceae fruit has optimized platelet aggregation inhibiting activity, comprising the steps of:

(a) preparing a start mix of homogenized fruit, wherein the start mix has a pH that does not exceed 5.5 and the start mix is held at a temperature that does not exceed 35° C.;

(b) separating a water soluble fraction from the start mix from insoluble solids of the start mix, wherein the water soluble fraction is obtained without raising the temperature of the fraction above 60° C.;

(c) filtering the water soluble fraction;

(d) removing free sugars from the filtered water soluble fraction with a food grade resin, wherein the resin adsorbs components from the fraction but does not adsorb free sugars, organic acids and salts, wherein the adsorbed components are recovered from the resin by elution with an ethanol/water mixture to provide a solution, and wherein ethanol is removed from the solution by evaporation under reduced pressure or by reverse osmosis; and (e) concentrating the solution to provide the extract of fruit of the Solanaceae family, wherein the extract is a concentrated aqueous solution containing <1% sugar and >95% of bioactive components contained in the start mix.

2. The method of claim 1, wherein the browning index of the start mix does not exceed 0.4 AU at 4% solids.

3. The method of claim 1, wherein the sugars are removed by resin-mediated separation.

4. The method of claim 1, wherein the extract is further processed into a powder.

5. The method of claim 1, wherein the start mix is diluted and comprises less than 33% solids.

* * * * *